(12) United States Patent
Warden et al.

(10) Patent No.: US 8,769,822 B2
(45) Date of Patent: Jul. 8, 2014

(54) METHOD FOR MANUFACTURING A DENTAL PROSTHESIS

(75) Inventors: Donne Joseph Warden, Green Bay, WI (US); Mark Ervin Olsen, Savage, MN (US); Brian Paul Wallenfelt, Plymouth, MN (US); Michael Craig Marshall, Prior Lake, MN (US); Minh Xuan Nguyen, Brooklyn Park, MN (US)

(73) Assignee: GeoDigm Corporation, Falcon Heights, MN (US)

( * ) Notice: Subject to any disclaimer, the term of this patent is extended or adjusted under 35 U.S.C. 154(b) by 53 days.

(21) Appl. No.: 13/301,441

(22) Filed: Nov. 21, 2011
(Under 37 CFR 1.47)

(65) Prior Publication Data
US 2012/0291284 A1    Nov. 22, 2012

Related U.S. Application Data

(60) Provisional application No. 61/415,684, filed on Nov. 19, 2010.

(51) Int. Cl.
*A61C 5/10*    (2006.01)
*B23P 13/00*    (2006.01)

(52) U.S. Cl.
USPC ............. 29/896.1; 29/559; 433/49; 433/223; 700/98

(58) Field of Classification Search
USPC ............. 29/896.1, 559; 433/49, 223; 700/98
See application file for complete search history.

(56) References Cited

U.S. PATENT DOCUMENTS

| | | | |
|---|---|---|---|
| 6,915,178 | B2 | 7/2005 | O'Brien et al. |
| 7,228,191 | B2 | 6/2007 | Hofmeister et al. |
| 7,463,942 | B2 | 12/2008 | O'Brien et al. |
| 7,735,542 | B2 | 6/2010 | Marshall et al. |
| 7,819,662 | B2 | 10/2010 | Marshall et al. |
| 7,877,160 | B2 | 1/2011 | O'Brien et al. |
| 8,280,542 | B2 | 10/2012 | O'Brien et al. |
| 2004/0265770 | A1* | 12/2004 | Chapoulaud et al. ........... 433/24 |
| 2005/0177261 | A1* | 8/2005 | Durbin et al. .................. 700/98 |
| 2007/0203600 | A1* | 8/2007 | Shibata et al. ................. 700/98 |
| 2007/0218426 | A1 | 9/2007 | Quadling et al. |
| 2009/0148816 | A1* | 6/2009 | Marshall et al. ............. 433/223 |

FOREIGN PATENT DOCUMENTS

WO    WO 2009/090214 A2    7/2009

OTHER PUBLICATIONS

International Search Report and Written Opinion mailed Feb. 6, 2012.

* cited by examiner

*Primary Examiner* — Alexander P Taousakis
(74) *Attorney, Agent, or Firm* — Merchant & Gould P.C.

(57) ABSTRACT

Dental prostheses may be manufactured based on electronic models of the prostheses. Manufacturing aids may be used to check manufacturing quality of the dental prosthesis and components thereof. For example, a jig may be used during and after the manufacture of the dental prostheses and systems and methods for using the same. A customized tooth die may be designed and fabricated to fit a dental prosthesis or components thereof in a jig for inspection. A customized jig may be designed and fabricated for inspecting a dental prosthesis or components thereof throughout the manufacturing process.

10 Claims, 22 Drawing Sheets

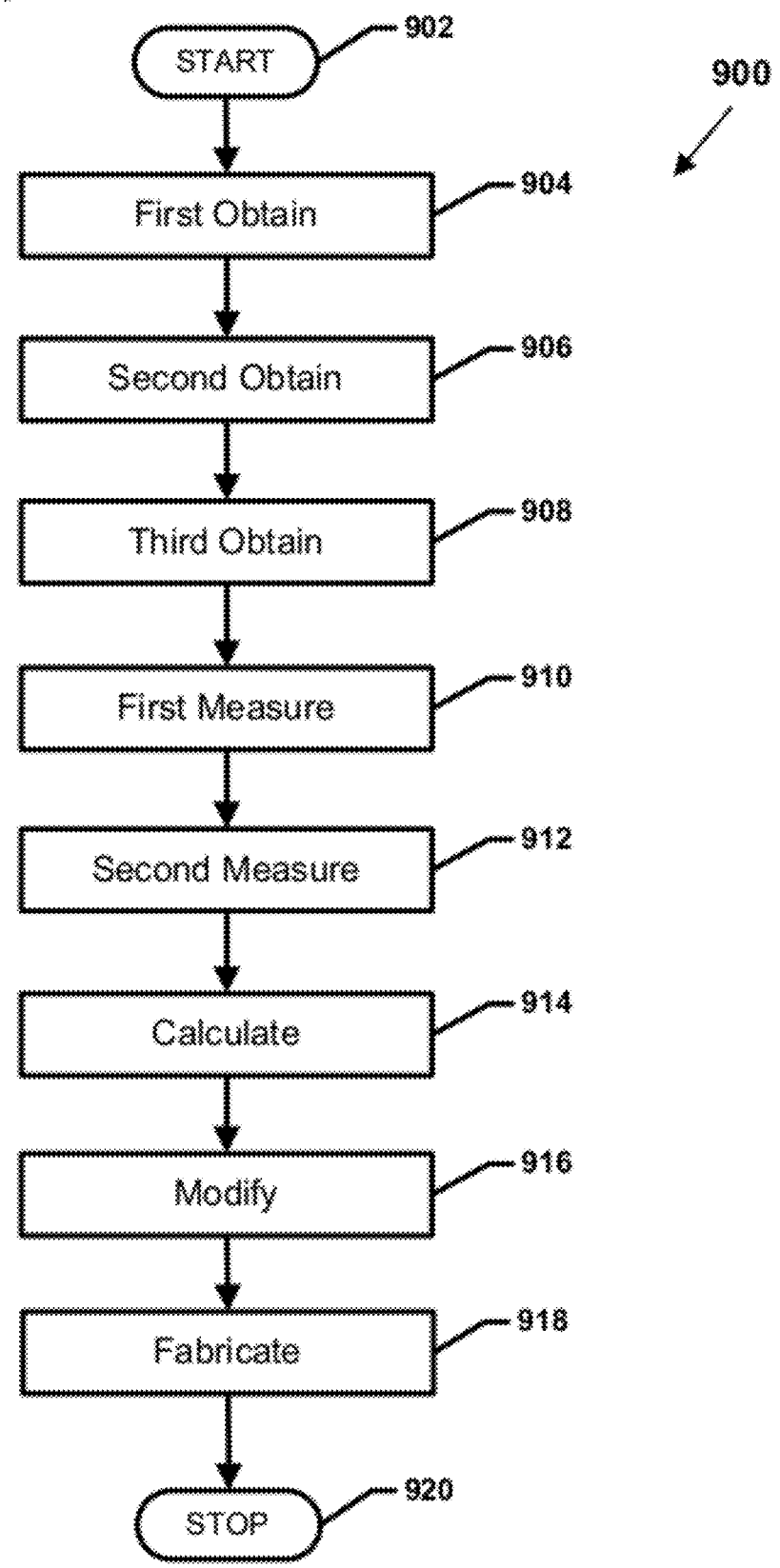

METHOD FOR MANUFACTURING A DENTAL PROSTHESIS

CROSS-REFERENCE PARAGRAPH

This application claims the benefit of U.S. Patent Application Ser. No. 61/415,684, filed Nov. 19, 2010, and titled "Dental Prosthesis Manufacturing Aids," the disclosure of which is hereby incorporated herein by reference in its entirety.

BACKGROUND

To produce dental prostheses (e.g., dental copings, dental crowns, etc.) to be mounted to a preparation site (e.g., a prepared tooth, an installed abutment, etc.) of a patient, technicians obtain electronic models of dentitions (e.g., the teeth and soft tissue surrounding the preparation site). In general, the technicians design electronic models of dental prostheses based on the electronic models of the dentitions.

In some prior systems, the technicians obtain impressions and/or plaster models of the dentitions from dentists or other dental/orthodontic professionals. The impressions and/or models can be scanned to produce electronic models of the dentitions. In other prior systems, electronic images can be obtained by directly scanning the mouths of the patients (e.g., using intra-oral scanners). The dental prostheses can be fabricated based on the electronic models. For example, in some prior systems, rapid prototyping techniques can be used to create casting patterns based on the electronic models. Such casting patterns can be used in forming casting molds using a lost-wax process. In other prior systems, milling techniques can be used to create either patterns of the dental prostheses or the dental prostheses themselves.

There exists a need in the art for improved manufacturing processes for dental prostheses.

SUMMARY

The disclosure relates to designing and fabricating manufacturing aids for use in a manufacturing dental prostheses. More particularly, the disclosure relates to the design and fabrication of partial physical models and jigs suitable for use at quality control check points. Some aspects of the disclosure relate to manufacturing a customized tooth die to fit a dental prosthesis or components thereof in a generic jig for inspection. Other aspects of the disclosure relate to manufacturing a customized jig for inspecting a dental prosthesis or components thereof.

BRIEF DESCRIPTION OF THE DRAWINGS

Referring to the drawing, wherein like numerals represent like parts throughout the several views:

FIG. 11 is a flowchart illustrating an operational flow for an example first customization process by which a custom tooth die can be designed and fabricated in accordance with the principles of the present disclosure;

DETAILED DESCRIPTION

The present disclosure provides for devices and techniques to aid in the manufacture of dental prostheses. In particular, the disclosure relates to customizable jigs and partial models and systems and methods for creating and using the same. Non-limiting examples of dental prostheses include dental restorations (e.g., dental crowns), dental bridges, dental abutments, and full or partial dentures.

Figure 1:
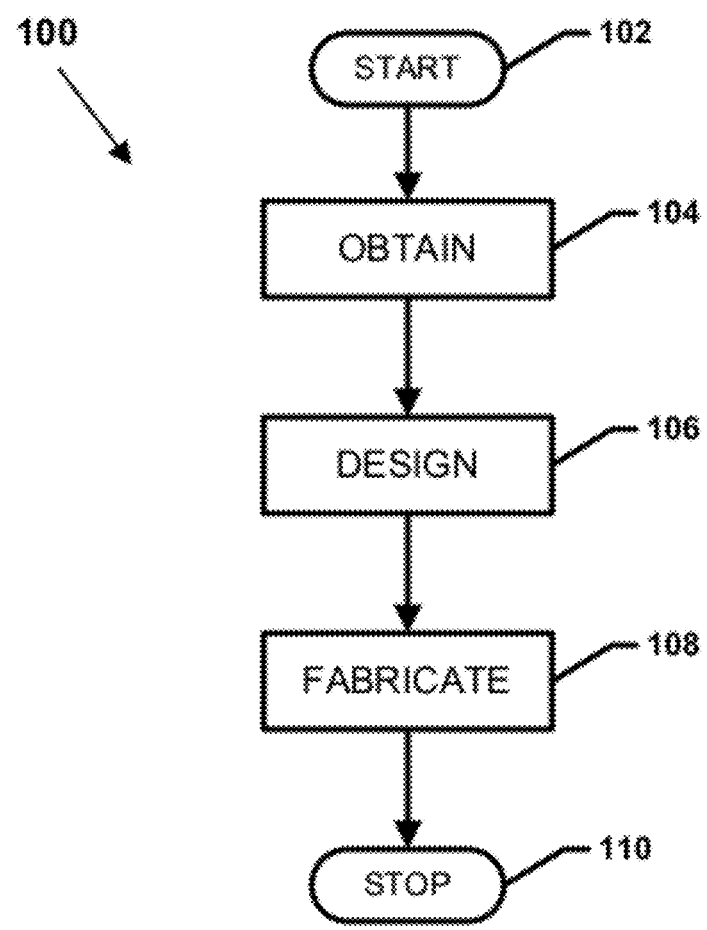
FIG. 1 is a flowchart illustrating an operational flow of an example production process for producing a dental prosthesis in accordance with the principles of the present disclosure.

FIG. 1 is a flowchart illustrating an operational flow of an example production process 100 for producing a dental prosthesis. The production process 100 performs any appropriate initialization procedures and begins at a start module 102. An obtain operation 104 acquires or receives an electronic model of a preparation site at which the dental prosthesis is to be mounted.

In accordance with some aspects, the obtain operation 104 acquires the electronic model by obtaining positional data representing the preparation site and generating the electronic model from the positional data. For example, in some implementations, the obtain operation 104 obtains positional data by scanning the preparation site (e.g., using an intra-oral scanner). In other implementations, the obtain operation 104 obtains positional data by scanning a physical reproduction (e.g., an impression, a plaster cast, or a stone model) of the preparation site. One such example system is described in more detail in U.S. Pat. Nos. 6,217,334, 6,206,693, 6,200,135, the disclosures of which are hereby incorporated by reference herein. In other implementations, the obtain operation 104 obtains positional data using a CT, CAT, MRI, or other type of bodily scan.

In accordance with some aspects, the preparation site includes at least one prepared tooth on which the dental prosthesis is to be mounted. In certain implementations, the preparation site includes multiple prepared teeth on which the dental prosthesis (e.g., a bridge) is to be mounted. In accordance with other aspects, the preparation site includes soft tissue (e.g., the gingival surface) surrounding the prepared tooth). In accordance with other aspects, the preparation site includes all or part of the surrounding dentition of the patient (e.g., teeth that are adjacent and/or antagonistic to the prepared tooth).

Figure 2:
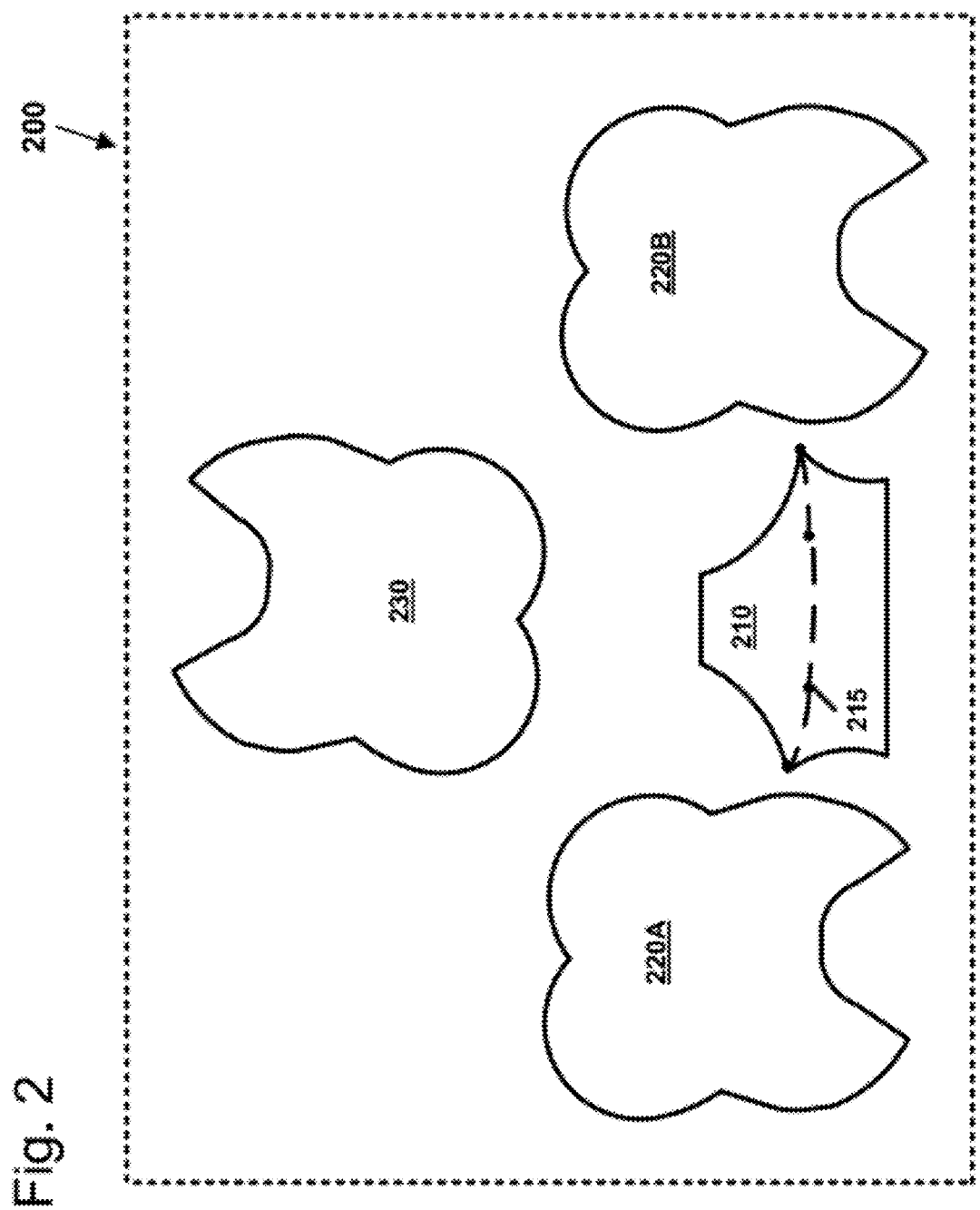
FIG. 2 is a diagram showing a simplified example electronic model of a dentition of a patient in accordance with the principles of the present disclosure.

For example, FIG. 2 is a diagram showing a simplified example electronic model 200 of a partial dentition of a patient acquired in the obtain operation 104. The dentition model 200 includes a prepared tooth 210 on which the dental prosthesis is to be mounted. For example, the dental prosthesis can be mounted over a margin curve 215 defined on the prepared tooth. In some implementations, the dentition model 200 includes at least a first adjacent tooth 220A (e.g., a mesial adjacent tooth or a distal adjacent tooth). In some implementations, the dentition model 200 also can include at least a second adjacent tooth 220B on an opposite side of the prepared tooth 210 from the first adjacent tooth 220A. In certain implementations, the dentition model 200 also can include one or more antagonistic teeth 230 that would interact with an occlusal surface of the dental prosthesis.

A design operation 106 of the production process 100 creates an electronic model 300 of the dental prosthesis based at least in part on the dentition model 200. For example, in some implementations, the prosthesis model 300 is generated by deforming or otherwise modifying a portion of the dentition model 200 or a copy thereof to form a suitable shape. In other implementations, the prosthesis model 300 is generated based on a library of generic models (e.g., a generic molar, a generic anterior, etc.) and modified to fit the preparation site and surrounding anatomy of the dentition model 200. In other implementations, the prosthesis model 300 includes portions that are modified from standard models and portions that are custom generated based on the dentition model 200.

In accordance with some implementations, the dental prosthesis includes a dental restoration. In some such implementations, the dental restoration includes a single-piece crown. In other such implementations, the dental restoration includes a multi-piece crown (e.g., a crown having a labial piece and a lingual piece). In other such implementations, the dental restoration includes a dental crown seated on a coping. In other implementations, the dental prosthesis includes a dental bridge including one or more restorations connected via a bridge framework. In other implementations, the dental prosthesis includes an abutment including a restoration and a tooth substitute that is configured to be installed in a jaw of a patient.

Figure 3:
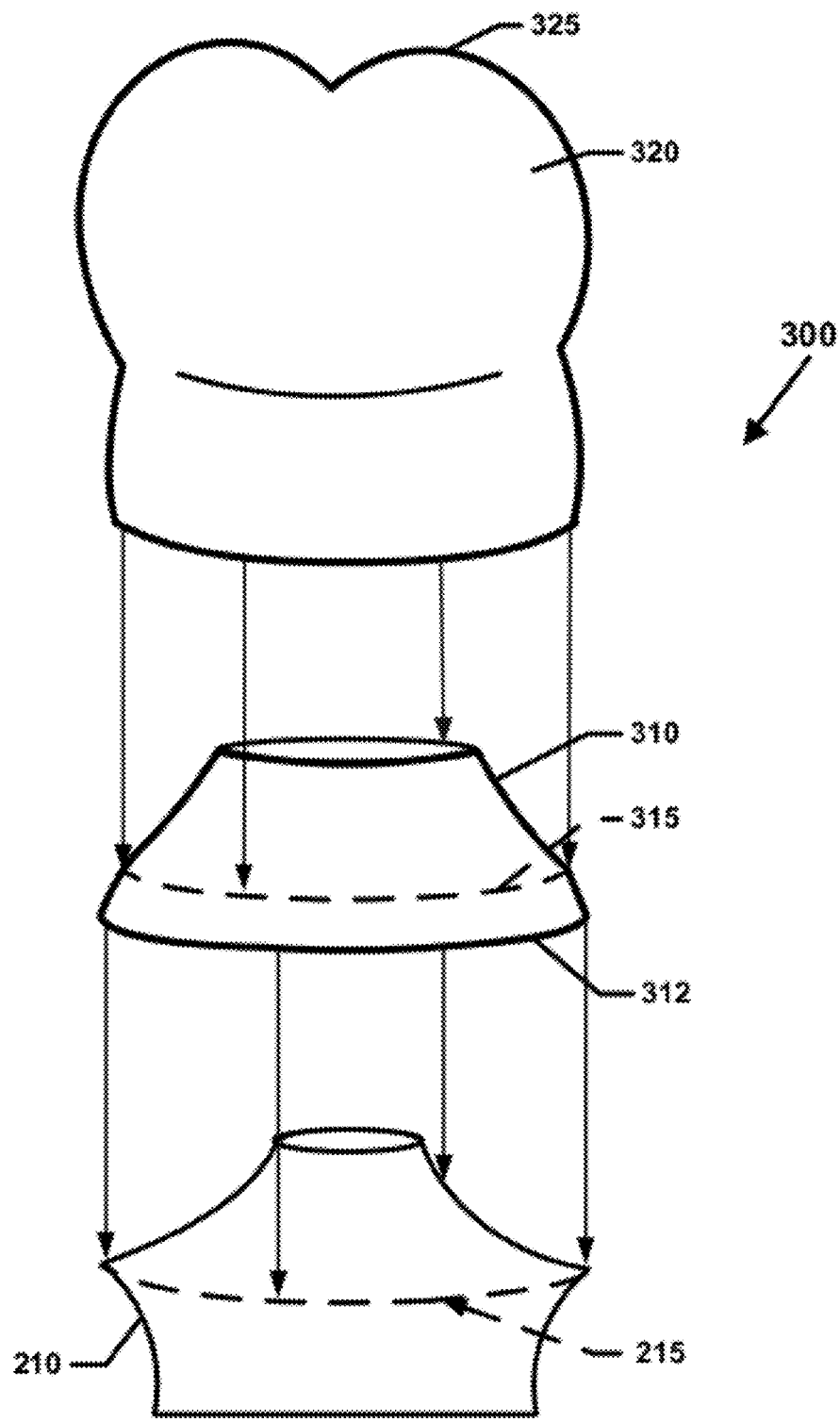
FIG. 3 is a diagram showing a simplified example electronic model of a dental prosthesis including a coping designed to fit the preparation site and a crown designed to fit the coping in accordance with the principles of the present disclosure.

FIG. 3 is a diagram showing a simplified example electronic model 300 of a dental prosthesis including a coping designed to fit the preparation site and a crown designed to fit the coping. In other implementations, however, the electronic model 300 may show a single-piece dental prosthesis. In some implementations, the prosthesis model 300 includes multiple electronic models of prosthesis components. For example, the prosthesis model 300 can include a coping model 310 and a crown model 320. The models 310, 320 can interact with each other to enable a technician to determine an appropriate spacing between the models. In one implementation, the prosthesis model 300 includes a coping 310, a crown 320, a gap between the coping 310 and the prepared tooth 210 sufficient to fit dental adhesive, and a gap between the coping 310 and the crown 320 sufficient to fit an opaque coating on the coping 310. The prosthesis model 300 also can be superimposed onto the dentition model 200 to enable a technician to observe interactions between the prosthesis and the dentition.

Non-limiting example processes and systems for designing dental prostheses can be found in U.S. Pat. No. 7,228,191 and U.S. Publication Nos. 2006-0115795, 2008-0220395, 2009-0148816, the disclosures of which are hereby incorporated by reference herein.

A fabricate operation 108 of the production process 100 creates the physical dental prosthesis 440 based on the prosthesis model 300. In accordance with some implementations, the fabricate operation 108 directly forms the physical prosthesis 440 from the prosthesis model 300. For example, in some implementations, the fabricate operation 108 mills the dental prosthesis 440 from a block of material (e.g., metal, plastic, plaster, gypsum, ceramic, acrylic, zirconium, etc.) In other implementations, the fabricate operation 108 prints the dental prosthesis 440, for example, using polymer printing, stereolithography, sintered powered metal, or other deposition-style processes. In still other implementations, the fabricate operation 108 prints a pattern of the dental prosthesis 440 that can be used to form a mold from which the dental prosthesis 440 or components thereof can be cast or pressed.

In some implementations, the fabricate operation 108 forms the dental prosthesis as a unitary piece. In other implementations, however, the fabricate operation 108 creates the dental prosthesis in separate, physical components. For example, in some implementation, the fabricate operation 108 forms the coping before forming the crown. In one implementation, the fabricate operation 108 mills a coping and prints out a pattern of the crown. The fabricate operation 108 seals the crown pattern to the coping, forms a mold, and presses the crown top onto the coping. In another implementation, the fabricate operation 108 casts the coping (e.g., from a printed pattern) instead of milling. In another implementation, the fabricate operation 108 builds the coping using a deposition process, such as powder sintered metal. In another implementation, the fabricate operation forms the crown top in multiple pieces.

The production process 100 performs any appropriate completion procedures and ends at a stop module 110.

Figure 4:
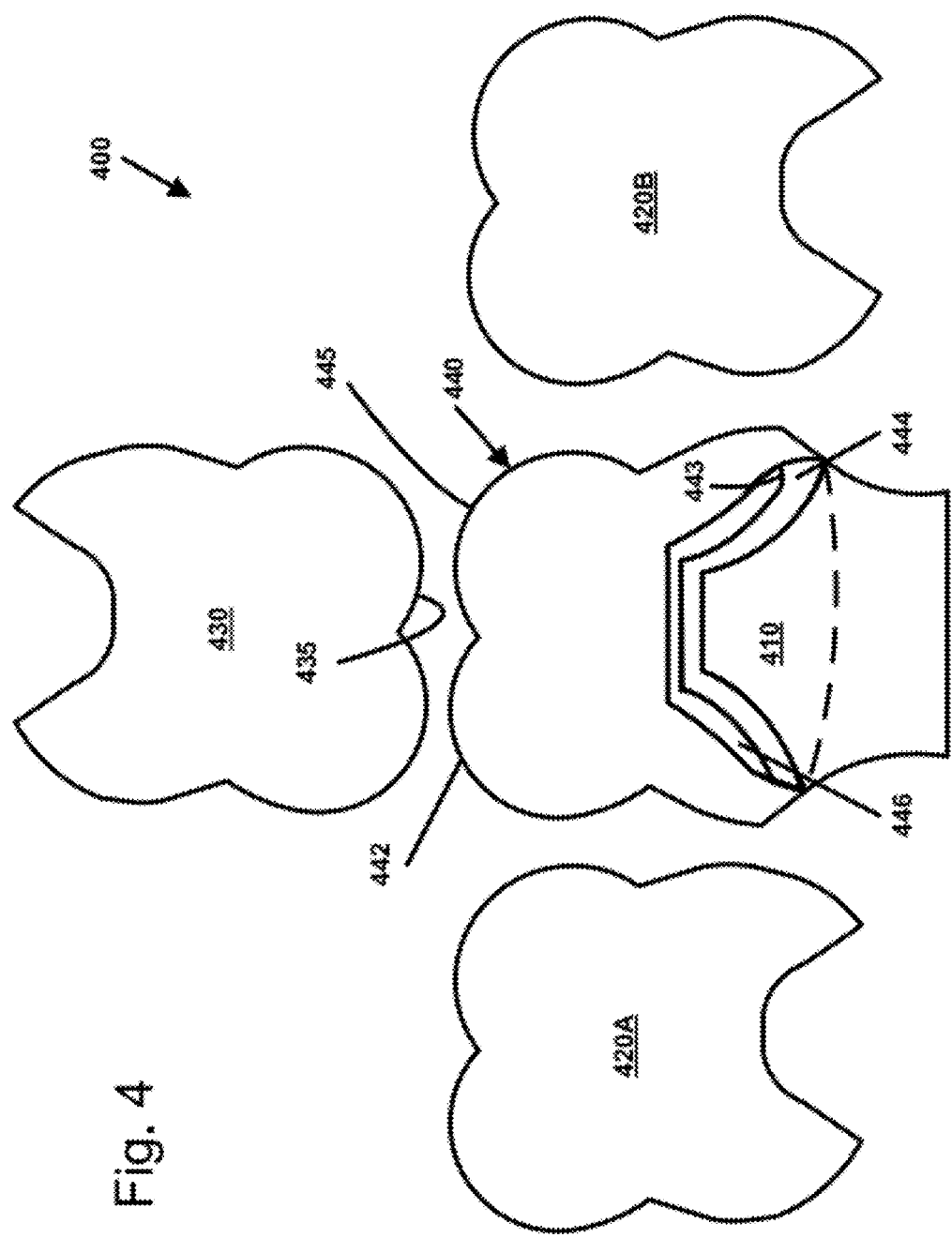
FIG. 4 is a diagram showing the fabricated dental prosthesis mounted to the preparation site in accordance with the principles of the present disclosure.

FIG. 4 is a diagram showing the fabricated dental prosthesis 440 mounted to a prepared tooth 410 at the preparation site. In the example shown, the dental prosthesis 440 includes a crown top 442, a coping 444, and an opaque coating 446 on the coping 444. In other implementations, however, the dental prosthesis can be formed as a single piece or from different components. The dental prosthesis 440 fits between mesial and distal adjacent teeth 420A, 420B. An occlusal surface 445 of the dental prosthesis 440 interacts with an occlusal surface 435 of the antagonistic tooth 430.

Figure 5:
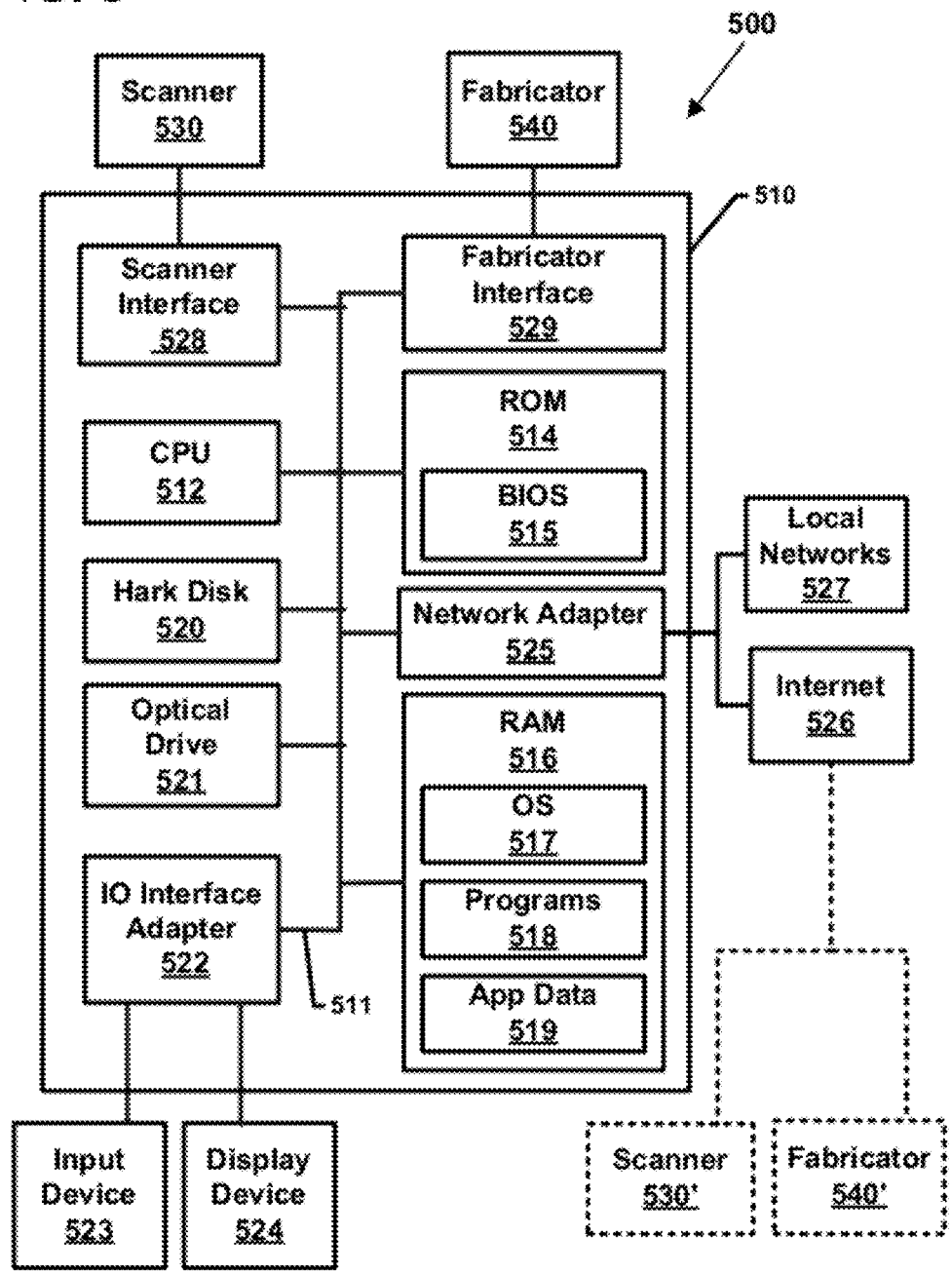
FIG. 5 illustrates an example design and production system on which example processes of the present disclosure can be executed according to one implementation of the present disclosure.

FIG. 5 illustrates an example design and production system 500 on which example processes of the present disclosure can be executed. In general, the system 500 includes a computing system 510 and a fabrication device 540 coupled to the computing system 510. The computing system 510 is configured to implement the design operation 106 of FIG. 1 and generate electronic models. The computing system 510 also is configured to convert the electronic models into a file format the fabrication device 540 can process. The fabrication device 540 is configured to implement the fabricate operation 108 of FIG. 1 and produce (e.g., print, mill, etc.) objects (e.g., prosthesis components, patterns of prosthesis components, dentition models or portions thereof, etc.) based on the electronic models generated by the computing system 510.

One example of the computing system 510 includes a processor unit 512, read only memory (ROM) 514, random access memory (RAM) 516, and a system bus 511 that couples various system components including the RAM 516 to the processor unit 512. The system bus 511 may be any of several types of bus structures including a memory bus or memory controller, a peripheral bus and a local bus using any of a variety of bus architectures. A basic input/output system 515 (BIOS) is stored in ROM 514. The BIOS 515 contains basic routines that help transfer information between elements within the computing system 510.

The computing system 510 can further include a hard disk drive 520 for reading from and writing to a hard disk, a magnetic disk drive (not shown) for reading from or writing to a removable magnetic disk, and/or an optical disk drive 521 for reading from or writing to a removable optical disk such as a CD ROM, DVD, or other type of optical media. The hard disk drive 520, magnetic disk drive, and optical disk drive 521 can be connected to the system bus 511 by a hard disk drive interface (not shown), a magnetic disk drive interface (not shown), and an optical drive interface (not shown), respectively. The drives and their associated computer-readable media provide nonvolatile storage of computer readable instructions, data structures, programs, and other data for the computing system 510.

Although the example environment described herein employs a hard disk drive 520, a removable magnetic disk, and removable optical disk drive 521, other types of computer-readable media capable of storing data can be used in the example system. Non-limiting examples of these other types of computer-readable mediums that can be used in the example operating environment include magnetic cassettes, flash memory cards, digital video disks, solid state disk drives, and Bernoulli cartridges.

A number of program modules may be stored on the ROM 514, RAM 516, hard disk drive 520, magnetic disk drive, or optical disk drive 521, including an operating system 517, one or more application programs 518, other program modules, and program (e.g., application) data 519.

A user may enter commands and information into the computing system 510 through input devices 523, such as a keyboard, touch screen, Haptic interface, and/or mouse (or other pointing device). Examples of other input devices 523 may include a microphone, joystick, game pad, satellite dish, haptic interface, and document scanner. These and other input devices are often connected to the processing unit 512 through an I/O port interface 522 that is coupled to the system bus 511. Nevertheless, these input devices 523 also may be connected by other interfaces, such as a parallel port, game port, or a universal serial bus (USB). A monitor 524 or other type of display device is also connected to the system bus 511 via an interface, such as the IO interface 522. In addition to the display device 524, computing systems typically include other peripheral output devices (not shown), such as speakers and document printers.

The computing system 510 may operate in a networked environment using logical connections to one or more remote computers. The remote computer may be a personal computer, a server, a router, a network PC, a peer device or other common network node, and typically includes many or all of the elements described above relative to the computing system 510. In certain embodiments, the network connections can include a local area network (LAN) or a wide area network (WAN). Such networking environments are commonplace in offices, enterprise-wide computer networks, intranets, and the Internet 526.

When used in a WAN networking environment, the computing system 510 typically includes a modem, Ethernet card, or other such means for establishing communications over the wide area network, such as the Internet 526. The modem or other networking components, which may be internal or external, can be connected to the system bus 511 via a network interface or adapter 525. When used in a LAN networking environment, the computing system 510 is connected to the local network 527 through the network interface 525. In a networked environment, program modules depicted relative to the computing system 510, or portions thereof, may be stored in the remote memory storage device. It will be appreciated that the network connections shown are exemplary and other means of establishing a communications link between the computers may be used.

In certain embodiments, the fabrication device 540 includes a rapid prototyping machine configured to print wax patterns. One example of such a rapid prototyping machine is the Projet™ wax printer from 3D Systems of South Carolina. In other implementations, the fabricator device 540 may be a CNC milling machine. In other implementations, the fabricator device 540 may be stereolithography machine. However, any type of fabrication device 540 may be used without deviating from the spirit and scope of the disclosure. In certain embodiments, the fabrication device 540 can be connected to the computing system 510 via an appropriate interface 529. Alternatively, a remote fabricator 540' may be connected to the computing system 510 via a network, such as the Internet 526.

The interface 529 can connected to the bus 511 such that the electronic model data may be retrieved from the appropriate or desired memory location. In some embodiments, the interface 529 converts the electronic models generated on the computing system 510 to a format readable by the fabrication device 540. In one example implementation, the interface 529 converts the electronic model to an STL file. The converted file can be transmitted to the fabrication device 540 using a direct line connection or using a networked connection described above.

In certain implementations, the design and production system 500 also includes a scanner 530 configured to obtain data upon which the generated electronic models are based. For example, a three-dimensional scanner 530 can be connected to the computing system 510 via an appropriate scanner interface (e.g., a USB port or other cable port) 528. Alternatively, a remote scanner 530' may be connected to the computing system 510 via a network, such as the Internet 526. The scanner interface 528 is connected to the bus 511 such that the scanned data may be stored in the appropriate or desired memory location, manipulated by the CPU 512, displayed on the display device 524, etc. Non-limiting examples of suitable scanners include a laser line scanner arranged and configured for scanning dental study casts (e.g., plaster casts) and an intra-oral scanner configured for scanning anatomy within a patient's mouth. However, any suitable scanner 530 may be used and a number of other methodologies might be employed to generate the scanned image data.

Portions of the preferred embodiment constructed in accordance with the principles of the present invention utilize a computer and are described herein as implemented by logical operations performed by a computer. The logical operations of these various computer implemented processes are generally performed either (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 6:
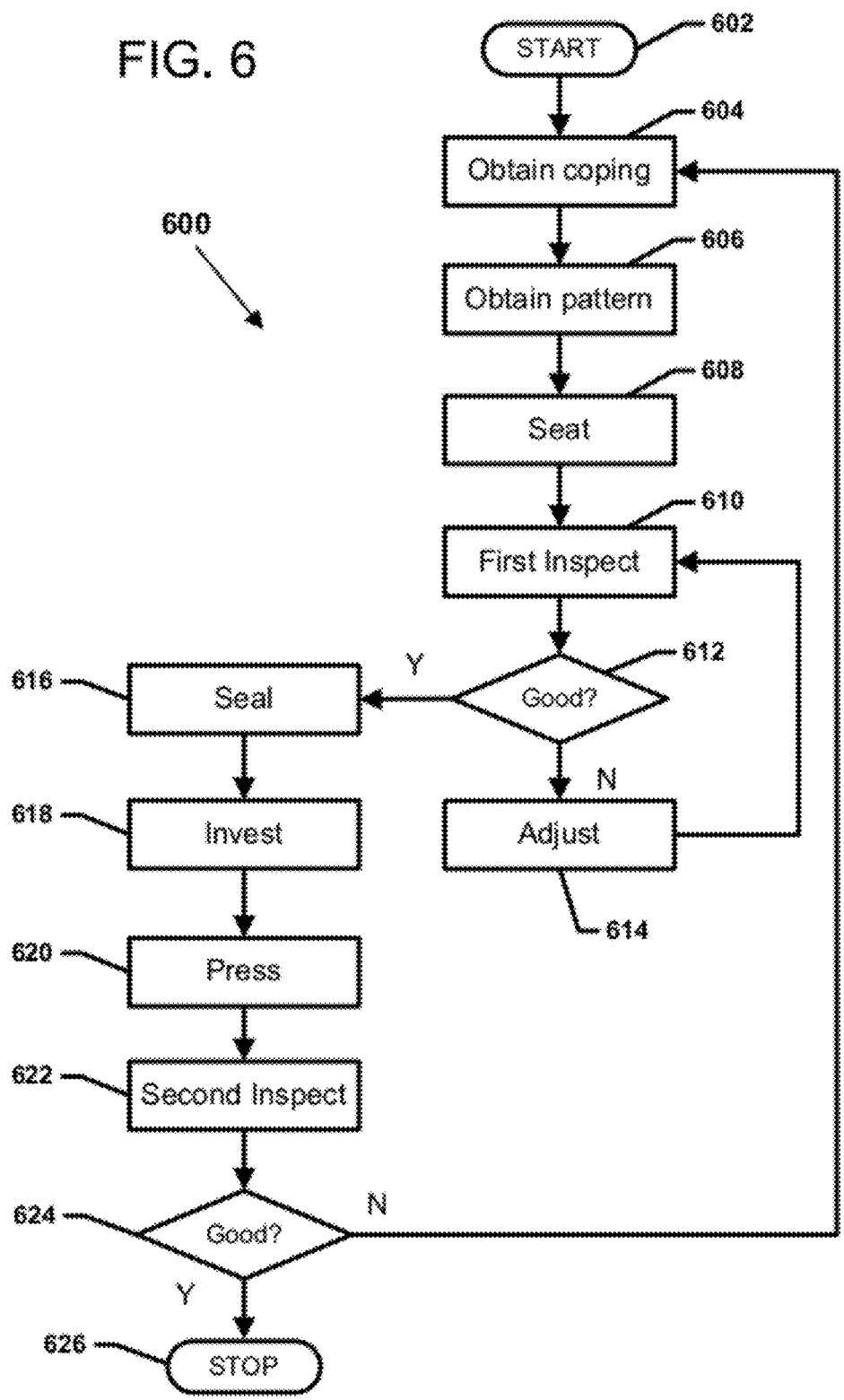
FIG. 6 is a flowchart illustrating an operational flow for one example fabrication process for producing a dental prosthesis based on an electronic model of the dental prosthesis in accordance with the principles of the present disclosure.

FIG. 6 is a flowchart illustrating an operational flow for one example fabrication process 600 by which the fabrication operation 108 of FIG. 1 can be implemented to produce a dental prosthesis based on an electronic model of the dental prosthesis. The fabrication process 600 performs any appropriate initialization procedures and begins at a start module 602. The fabrication process 600 obtains a dental coping at a first obtain operation 604 and a pattern of a dental crown at a second obtain operation 606.

In accordance with some implementations, the first obtain operation 604 obtains the dental coping by milling the coping from an electronic model of the coping. In accordance with other implementations, the first obtain operation 604 obtains the dental coping by printing a pattern of the coping based on an electronic model of the coping and casting the coping using the pattern. In accordance with other implementations, the first obtain operation 604 directly prints or builds the dental coping (e.g., using a deposition or stereo lithography process). In accordance with other implementations, the first obtain operation 604 receives the dental coping from a third party. In one implementation, the dental coping includes an opaque coating.

In accordance with some implementations, the second obtain operation 606 obtains the pattern of the crown top by printing the pattern (e.g., using polymer/wax printing, stereo lithography, or other deposition techniques) based on an electronic model of the pattern. In accordance with other implementations, the second obtain operation 606 obtains the pattern of the crown top by manually forming the pattern (e.g., by hand). In accordance with other implementations, the second obtain operation 606 receives the crown-top pattern from a third party.

A seat operation 608 arranges the crown-top pattern on the dental coping to form a fabrication assembly. In some implementations, the crown-top pattern is positioned to leave a gap between the exterior surface of the dental coping and the inner surface of the crown-top pattern. In other implementations, the crown-to pattern is positioned so that the inner surface of the pattern contacts the exterior surface of the coping. In certain implementations, the crown-top has a specific rotational orientation relative to the coping in order to seat appropriately.

An inspection operation 610 determines whether the crown-top pattern is appropriately seated on the dental coping. In some implementations, the inspection operation 610 is implemented by a technician who determines whether the crown-top is seated appropriately based on a visual examination of the fabrication assembly. In other implementations, the inspection operation 610 obtains positional data of the fabrication assembly (e.g., via a scanning device), generates an electronic model of the fabrication device using the positional data, and compares the electronic model of the fabrication device with the electronic model of the dental prosthesis. In other implementations, the inspection operation 610 is implemented using a jig, for example, as described in more detail below.

A first determination module 612 determines whether the crown-top pattern was found to be seated correctly during the inspection operation 610. If the crown-top pattern is determined to be seated incorrectly, then an adjust operation 614 modifies the fabrication assembly to reseat the crown-top pattern on the dental coping and the fabrication process 600 cycles back to the inspection operation 610.

In some implementations, the adjust operation 614 modifies the placement (e.g., height and/or rotational orientation) of crown-top pattern on the coping. In other implementations, the adjust operation 614 modifies the structure of the pattern (e.g., adding material to a base of the pattern to add height to the crown-top or by grinding away material from the base of the pattern). In other implementations, the adjust operation 614 modifies the dental coping (e.g., by adding more opaque coating or grinding off portions of the coping).

If the first determination module 612 determines that the crown-top pattern is seated correctly on the dental coping, however, then a seal operation 616 attaches the crown-top pattern to the dental coping. In accordance with some aspects, the seal operation 616 attaches the pattern to the coping with sufficient strength to enable the fabrication assembly to be invested to make a mold with which to cast or press the crown-top. In accordance with some implementations, the seal operation 612 is implemented by a technician who applies wax or other deformable material. In other implementations, the seal operation 612 is implemented using adhesive.

An invest operation 618 creates a mold from the fabrication assembly after the crown pattern is sealed to the coping. For example, in the invest operation 618, the technician can place the fabrication assembly within a container and fill the container with investment material. When the investment material hardens, the crown pattern is eliminated to form the mold. A press operation 620 creates the crown by pressing ceramic or other appropriate material into the crown pattern-shaped void in the mold. In certain implementations, the ceramic material is pressed onto the dental coping that is held within the mold to form the dental prosthesis. In other implementations, only the pattern is invested; the crown is formed separately from the coping and later assembled.

A second inspect operation 622 determines whether the dental prosthesis is acceptable (e.g., whether the prosthesis will fit the preparation site, whether the prosthesis is capable of being installed on the preparation site, whether the prosthesis is visually appealing, etc.). For example, the second inspect operation 622 can determine whether the invest operation 618 and/or press operation 620 resulted in any manufacturing errors (e.g., air pockets resulting in deformation of the crown). The second inspect operation 622 also can serve as a final test of how the design of the dental prosthesis will interact with the rest of the patient's dentition.

In some implementations, the second inspection operation 622 is implemented by a technician who performs a visual examination of the dental prosthesis. In other implementations, the second inspection operation 622 obtains positional data of the dental prosthesis (e.g., via a scanning device), generates an electronic model of the fabricated dental prosthesis using the positional data, and compares the electronic model of the fabricated prosthesis with the electronic model of the designed dental prosthesis. In other implementations, the inspection operation 622 is implemented using a jig, for example, as described in more detail below.

A second determination module 624 determines whether the dental prosthesis was found to be manufactured within reasonable tolerances during the second inspect operation 622. If the second determination module 624 determines the dental prosthesis is not acceptable, then the fabrication process 600 cycles back to the beginning to repeat again. In certain implementations, a technician may choose to redo the fabrication process. In other implementations, the technician may choose to modify the design of the dental prosthesis before attempting fabrication again.

When the second determination module 624 determines the dental prosthesis is acceptable for delivery to the dentist and installation on the patient, the fabrication process 600 performs any appropriate completion procedures and ends at a stop module 626.

Figure 7:
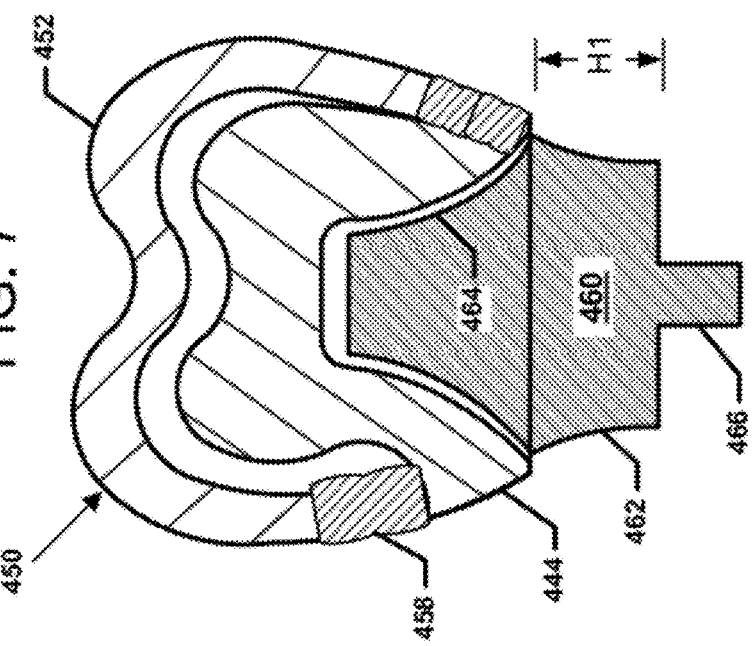
FIG. 7 is a diagram showing an example crown-top pattern mounted to a dental coping to form a fabrication assembly in accordance with the principles of the present disclosure.

FIG. 7 is a diagram showing an example crown-top pattern 452 mounted to a dental coping 444 to form a fabrication assembly 450. In the example shown, the crown-top pattern 452 is sealed to the dental coping 444 using portions 458 of wax or other material. In other implementations, the portions 458 sealing the pattern 452 to the coping 444 can be formed from other types of materials.

In some implementations, at least a portion of the crown-top pattern 452 is positioned on a collar 443 of the dental coping 444. In other implementations, at least a portion of the crown-top pattern covers at least a substantial portion of the dental coping 444. For example, a labial side of a crown-top pattern 452 may extend over the labial side of a corresponding coping 444 while a lingual side of the crown-top 452 seats on a coping collar 443 (see FIG. 7).

In the example shown, the fabrication assembly 450 also includes a tooth die 460 on which the coping 444 can be positioned. In general, the tooth die 460 is a physical model of the prepared tooth 410 or portion thereof. The tooth die 460 includes a base 462 having a height H1 (see FIG. 7). The tooth die 460 also includes an abutment section 464 on which the dental coping is mounted. In one implementation, the abutment surface 464 generally matches the surface of the prepared tooth 410 on which the dental prosthesis 440 is to be mounted.

In certain implementations, the tooth die 460 also may include a mounting flange 466 that facilitates mounting the tooth die 460 to a surface (e.g., by inserting the mounting flange 466 into a complementary hole in the surface). In one implementation, the abutment section 464 extends from a first side of the base 462 and the mounting flange 466 extends from a second side of the base 462. In other implementations, the tooth die 460 defines a hole or recess, instead of a mounting flange, that can fit a peg or other mounting protrusion. In still other implementations, the surface to which the tooth die 460 is mounted defines one or more holes in which a dowel may be selectively received. In some such implementations, the tooth die 460 includes a dowel that may be inserted into one of the holes to position the tooth die 460 on the surface. In other such implementations, a dowel may be mounted to the tooth die 460 (e.g., via insertion into an opening defined by the tooth die 460) and may be mounted to the surface at one of the holes. In still other implementations, one of the tooth die 460 and the surface define a notch at which the other may be mounted.

Figure 8:
FIG. 8 illustrates one example transverse cross-sectional profile shape for the mounting flange in accordance with the principles of the present disclosure.

In certain implementations, the mounting flange 466 has a shape that is not rotationally uniform. More specifically, in certain implementations, the mounting flange 466 is shaped so that the mounting flange 466 fits into a complementary hole in only one rotational orientation. FIG. 8 illustrates one example transverse cross-sectional profile shape for the mounting flange 466. In other implementations, the mounting flange 466 may have different non-uniform transverse cross-sectional profiles. In still other implementations, however, the mounting flange 466 can be symmetrical or uniform.

Figure 9:
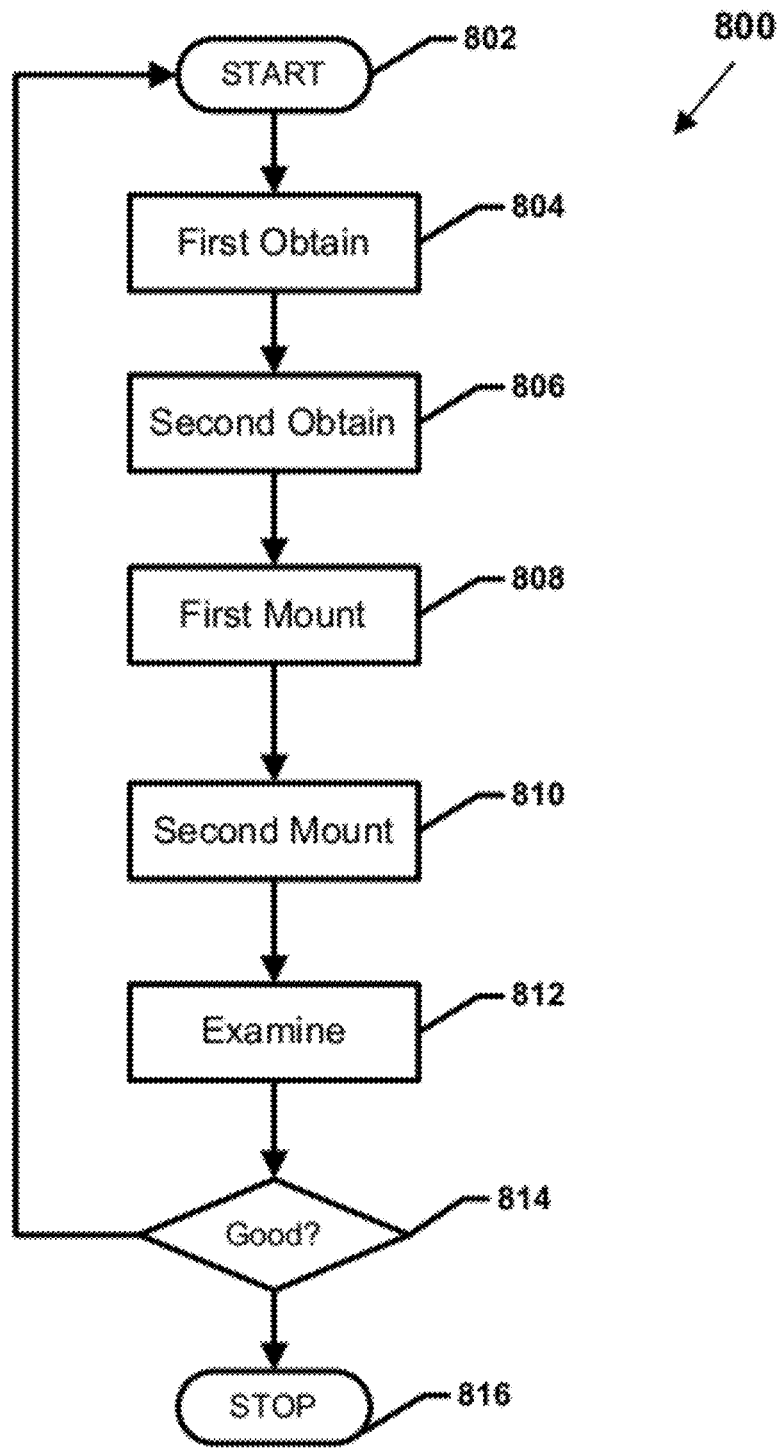
FIG. 9 is a flowchart illustrating an operational flow for an example inspection process by which one or more parameters of a fabrication assembly can be compared against expected values using a jig in accordance with the principles of the present disclosure.

FIGS. 9-20 illustrate some example devices and processes for inspecting a fit between a coping and a crown or crown pattern. For example, the devices and processes may be utilized to implement the first inspection operation 610 and/or the second inspection process 622 of the fabrication process 600. FIG. 9 is a flowchart illustrating an operational flow for an example inspection process 800 by which one or more parameters of a fabrication assembly, such as fabrication assembly 450, or a dental prosthesis, such as prosthesis 440, can be compared against expected values using a jig.

For example, in some implementations, the inspection process 800 determines that a crown pattern 452 is correctly seated on a coping 444 if the parameters of the fabrication assembly 450 are within acceptable ranges of the expected values prior to fabricating the crown. For example, the inspection process 800 may be performed prior to finalizing the prosthesis (e.g., bonding the crown to the coping). In other implementations, the inspection process 800 determines that a fabricated crown (e.g., cast crown, pressed crown, milled crown, printed crown, etc.) is correctly seated on a fabricated coping (e.g., milled coping, cast coping, printed coping, pressed coping, etc.) if dimensions of the fabricated crown and coping seated together are within acceptable ranges of the expected values. For example, the inspection process 800 may be performed to a sampling of final appliances or all final appliances before delivery to a customer or user.

In accordance with some aspects of the disclosure, the inspection process 800 is implemented using a jig (which also can be referred to as a frame). For example, in some implementations, the jig facilitates checking the actual height of a fabrication assembly against an expected height of the fabrication assembly. In certain implementations, the expected height of the fabrication assembly is determined from the electronic model of the dental prosthesis. In other implementations, the jig can aid in judging other types of parameters (e.g., width, contouring, etc).

The inspection process 800 performs any appropriate initialization procedures and begins at a start module 802. A first obtain operation 804 acquires or receives a fabrication assembly 450 to be checked. In some implementations, the fabrication assembly 450 includes a dental coping 444 and a crown-top pattern 452. In other implementations, the fabrication assembly 450 also includes a tooth die 460 on which the coping 444 is positioned.

Figure 10:
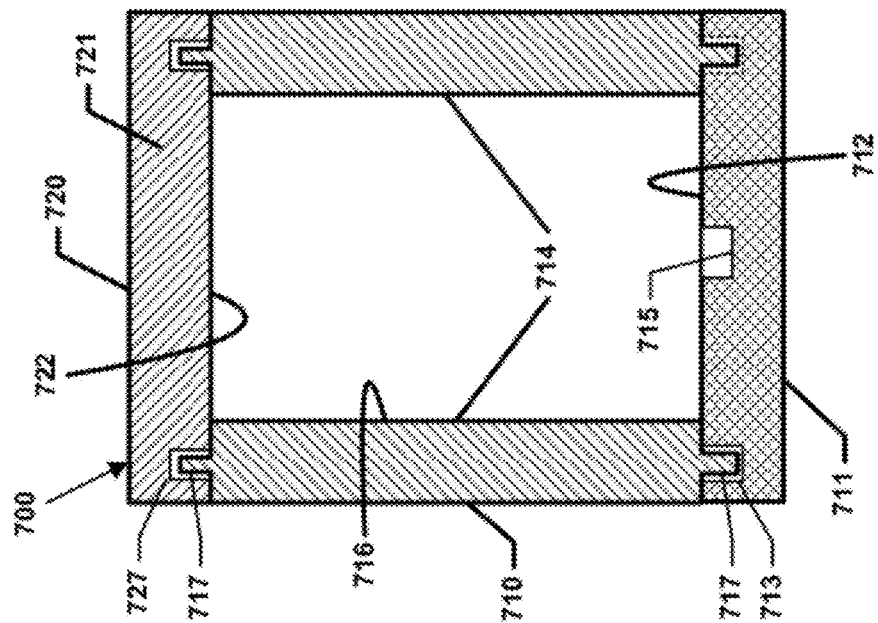
FIG. 10 is a cross-sectional view of one example jig suitable for use in the inspection process of FIG. 9 in accordance with the principles of the present disclosure.

A second obtain operation 806 acquires or receives a jig. FIG. 10 is a diagram of one example jig 700 suitable for use in the inspection process 800. The example jig 700 includes a base 710 and a cover 720. The base 710 includes a body 711 defining a seating section 712 on which a fabrication assembly, such as fabrication assembly 450, can be positioned. In some implementations, the seating section 712 defines a generally flat surface on which the fabrication assembly 450 can seat. In other implementations, the seating section 712 defines a recess 715 in which a portion of the fabrication assembly 450, such as mounting flange 466, can be inserted. In one implementation, the recess 712 is shaped so that the mounting flange 466 fits in the recess only when positioned in a specific rotational orientation.

The jig base 710 includes support members 714 on which the cover 720 can be mounted. The jig base 710 can include multiple support members 714 at spaced intervals along the base 710. For example, in some implementations, the jig base 710 includes a first support member 714 at a first side of the base 710 and a second support member 714 at a second, opposite side of the base 710. In other implementations, the support members 714 can be positioned at intermediate sections of the base 710. In still other implementations, the jig base 710 can include greater or fewer support members 714. For example, in some implementations, the jig base 710 also can include front and back support members.

In some implementations, the support members 714 are typically narrower than the fabrication assembly 450. In other implementations, however, the support members 714 can be wider than the fabrication assembly 450. In some implementations, at least an inwardly facing surface 716 of each support member 714 is planar. In other implementations, however, the inwardly facing surface 716 can be curved, angled, or contoured (as described in more detail below). In some implementations, the support members 714 are monolithically formed with the seating section 712 of the base 710 (see FIG. 13). In other implementations, the support members 714 are separate from the seating section 712 and can be mounted (e.g., via interlocking pegs and recesses or other such interfaces) and/or fastened (e.g., via brackets, screws, clamps, etc.) to the jig base 710. In the example shown in FIG. 10, the support members 714 include pegs 717 that fit in recesses 713 in the jig base body 711.

The cover 720 includes a body 721 defining an interface surface 722 that opposes the seating section 712 of the base 710 when the cover 720 is mounted to the base 710. In some implementations, the cover 720 defines a planar (e.g., flat) surface. In other implementations, the cover 720 defines a contoured surface. In one implementation, the cover 720 defines a surface that matches an occlusal surface of the crown pattern 452.

In some implementations, the cover 720 defines an interface arrangement 727 that fits with a complementary interface arrangement 717 of the base 710. In certain implementations, the interface arrangement 717 of the base 710 is formed at distal ends of the support members 714. For example, in some implementations, the cover 720 includes pegs 727 that are configured to be inserted into holes 717' (FIG. 13) defined in the support members 714 of the base 710. In other implementations, the cover 720 defines holes 727 that are configured to receive pegs 717 (FIG. 10) of the support members 714. In still other implementations, the interface arrangements 717, 727 define interlocking dove-tailed members, latching members, or releasable fasteners.

Figure 13:
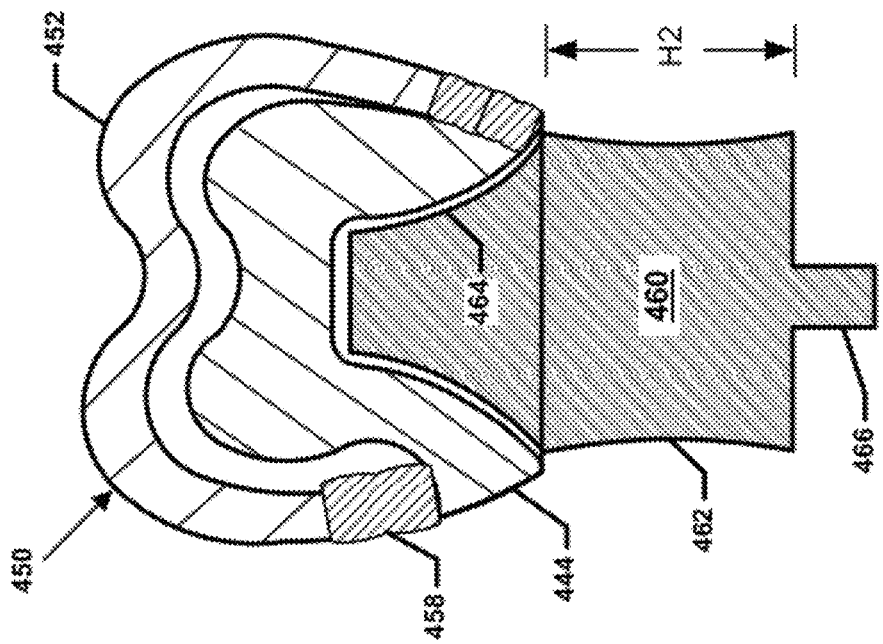
FIG. 13 is a cross-sectional view of the fabrication assembly of FIG. 12 with the customized tooth die installed on a jig.

A first mount operation 808 places the fabrication assembly 450 on the seating area 712 of the jig 700 (see FIG. 13). For example, in some implementations, the mounting flange 516 of the fabrication assembly 450 can be inserted into a complementary opening 715 defined in the jig base 710. In other implementations, a recess defined in the fabrication assembly 450 (e.g., in a bottom of the tooth die 510) can mount over a complementary mounting flange on the seating area 712 of the jig 700. In certain implementations, the fabrication assembly 450 is placed on the jig base 710 at a particular rotational orientation. In other implementations, the fabrication assembly 450 can be placed on the seating area 712 without any interlocks.

A second mount operation 810 positions the cover 720 of the jig 700 on the base 710 (see FIG. 13). In some implementations, the cover 720 is placed on the support members 714. In certain implementations, the interface arrangement 727 of the cover 720 fits with the complementary interface arrangement 717 of the base 710. For example, in one implementation, pegs extending downwardly from the cover 720 can slide into openings defined at distal ends of the support members 714. In another implementation, openings defined in the cover 720 can slide over pegs extending upwardly from the support members 714. In other implementations, the jig cover 720 can be otherwise mounted to the jig base 710.

An examine operation 812 ascertains whether one or more parameters of the fabrication assembly 450 are sufficiently close to expected values. For example, in some implementations, the examine operation 812 determines whether the height of the fabrication assembly 450 sufficiently matches an expected height. In one implementation, the examine operation 812 ascertains whether a top of the fabrication assembly 450 is sufficiently close to the interface surface 722 of the cover 720. In other implementations, the examine operation 812 also may determine whether sides of the fabrication assembly 450 are located within an acceptable distance from the support members 714.

A determination module 814 determines whether the examine operation 812 found the parameters of the fabrication assembly 450 to be acceptable. If the determination module 614 determines the fabrication assembly 450 to be acceptable, then the inspection process 800 ends at a stop module 816. If the determination module 814 determines the fabrication assembly 450 to be unacceptable, however, then the inspection process 800 cycles back to the start module 802 to begin again.

In accordance with some aspects, if the determination module 814 determines that the fabrication assembly 450 is too short (e.g., does not reach the cover interface surface 722 or is a sufficient distance away), then the first obtain operation 804 can reposition (e.g., raise) the crown pattern 452 on the dental coping 444 prior to sealing to the pattern to the coping. In accordance with other aspects, if the determination module 814 determines that the fabrication assembly 450 is too tall (e.g., inhibits installing the cover 720 on the support posts 714 or extends past the cover 720), then the first obtain operation 604 can modify (e.g., shorten by removing material) either the pattern 452 or the coping 444 prior to sealing.

In some implementations, the jig 700 can be custom designed to fit a specific fabrication assembly 450, as will be described in more detail herein. In other implementations, a generic jig 700 can be used with various fabrication assemblies 450. In certain implementations, a generic jig 700 can be produced in one or more standardized shapes and/or standardized sizes. Each fabrication assembly 450 can be modified to fit one of the generic jigs 700. For example, parameters of the tooth die 460 can be selected to appropriately position each fabrication assembly 450 within the jig 700. In one implementation, the height of the tooth die base 462 can be modified to position the coping 444 and crown top pattern 452 at an appropriate vertical position within the jig 700.

FIG. 11 is a flowchart illustrating an operational flow for an example first customization process 900 by which a custom tooth die 460 can be designed and fabricated for use with a particular fabrication assembly 450 or dental prosthesis 440 and a generic jig to inspect the fabrication assembly or a dental prosthesis. In accordance with aspects of the disclosure, the first customization process 900 can be used to implement the first obtain operation 804 of the inspection process 800. The first customization process 900 performs any appropriate initialization procedures and begins at a start module 902.

A first obtain operation 904 acquires or receives an electronic model of a tooth die 460 that can be used as part of the fabrication assembly 450. In the example shown in FIG. 7, the electronic model of the tooth die 460 includes the base 462, an abutment surface 464, and a mounting flange 466 as described above. In certain implementations, the tooth die model is generated based on a previously generated electronic model 200 of the patient's dentition. In some implementations, the electronic model of the tooth die 460 is pulled from a library of generic tooth die shapes and modified based on the dentition model 200. In other implementations, the electronic model of the tooth die 460 is copied or isolated from the dentition model 200. In still other implementations, a physical model of the dentition or portion thereof can be newly scanned to obtain the die model.

A second obtain operation 906 acquires or receives the electronic model representing the dental prosthesis, such as prosthesis model 300, to be manufactured. In some implementations, the second obtain operation 906 pulls the dental prosthesis model 300 from memory. For example, in some implementations, the dental prosthesis model 300 can be obtained from a third party, for example, via an electronic network (e.g., the Internet) or via a storage medium (e.g., a hard disk, an optical disc, a flash memory, etc.). In other implementations, the prosthesis model is designed (e.g., based on the dentition model 200 of FIG. 2) by a technician during or subsequent to the implementation of the first obtain operation 904.

As noted herein, the naming conventions used to designate the process steps do not imply a required execution sequence. For example, in some implementations, the dental prosthesis model of the second obtain operation 906 can be designed using the tooth die model of the first obtain operation 904. In other implementations, the tooth die model of the first obtain operation 904 can be designed using the dental prosthesis model of the second obtain operation 906.

A third obtain operation 908 acquires or receives a generic jig 700. In some implementations, the third obtain operation 908 acquires a physical jig 700. In other implementations, an electronic model of the jig 700 is obtained.

A first measure operation 910 determines a height of the jig 700. For example, the height of the jig 700 may be measured between the seating region 712 of the base 710 and the interface surface 722 of the cover 720. In some implementations, the first measure operation 910 can measure a height of the physical jig 700 (e.g., using a ruler, calipers, or other instrument for measuring length). In other implementations, the first measure operation 910 can measure a virtual height of the electronic model of the jig 700 (e.g., by calculating a distance between two points or two planes on the model using known techniques).

A second measure operation 912 determines an expected height of the dental prosthesis. In certain implementations, the second measure operation 912 determines the expected height by ascertaining a height of the electronic model 300 of the dental prosthesis 440. In some implementations, the expected height is ascertained by electronically measuring a distance between a point on the coping model 310 and a point on the crown model 320 of the prosthesis model 300. In other implementations, the height can be measured between two planes at least partially defined by the prosthesis model 300.

In some implementations, the point on the coping model is located along an interior surface of the coping model 310. In other implementations, the point on the coping is located along an interface perimeter 312 (see FIG. 3) of the coping model 310. In some implementations, the point on the crown is located on an occlusal surface 325 of the crown model 320. In one implementation, the points on the coping and crown models are each selected by a technician. In other implementations, the points are otherwise selected automatically by a computer. For example, in certain implementations, the lowest and highest points, respectively, on the models are automatically selected. In one implementation, the lowest and highest points are measured along an insertion axis followed by the restoration being installed on the coping.

A calculate operation 914 determines a suitable height H2 for the tooth die 460. The height H2 of the tooth die 460 is selected to hold the fabrication assembly 450 within the jig 700 so that the occlusal surface of an appropriately seated crown-top pattern 452 will be located within a tolerated range of distance from the interface surface 722 of the cover 720 based on the measured height of the jig and the expected height of the dental prosthesis.

For example, in accordance with certain aspects, the calculate operation 914 subtracts the height of the fabrication assembly 450 from the height of the jig 700 to obtain an appropriate height for the tooth die 460. In some implementations, the calculate operation 914 determines a suitable height for the entire tooth die 460. In other implementations, the calculate operation 914 determines a suitable height for the base body 462 of the tooth die 460.

A modify operation 916 adjusts the electronic model of the tooth die 460 to increase or decrease the height based on the results of the calculate operation 914. For example, in some implementations, if the calculate operation 914 determines the appropriate height of the tooth die 460 is greater than the height of the tooth die model, then the modify operation 916 may adjust the die model to lengthen the tooth die base 462 (e.g., compare height H1 of die base 462 of FIG. 7 to height H2 of die base 462 of 12). If the calculate operation 914 determines the appropriate height of the tooth die 460 is less than the height of the tooth die model, however, then the modify operation 916 may shorten the tooth die base 462.

A fabricate operation 918 produces the tooth die 460 based on the modified tooth die model. In some implementations, the tooth die 460 is milled from a block of material (e.g., metal, resin, plaster, wax, Renwood, etc.). In other implementations, the tooth die 460 is printed (e.g., polymer printing, stereolithography, sintered powered metal, or other deposition-style processes). In still other implementations, the fabricate operation 918 can print a pattern of the tooth die 460 and cast the tooth die 460 from the pattern as discussed above with respect to the crown.

The first customization process 900 performs any appropriate completion procedures and ends at a stop module 920.

Figure 12:
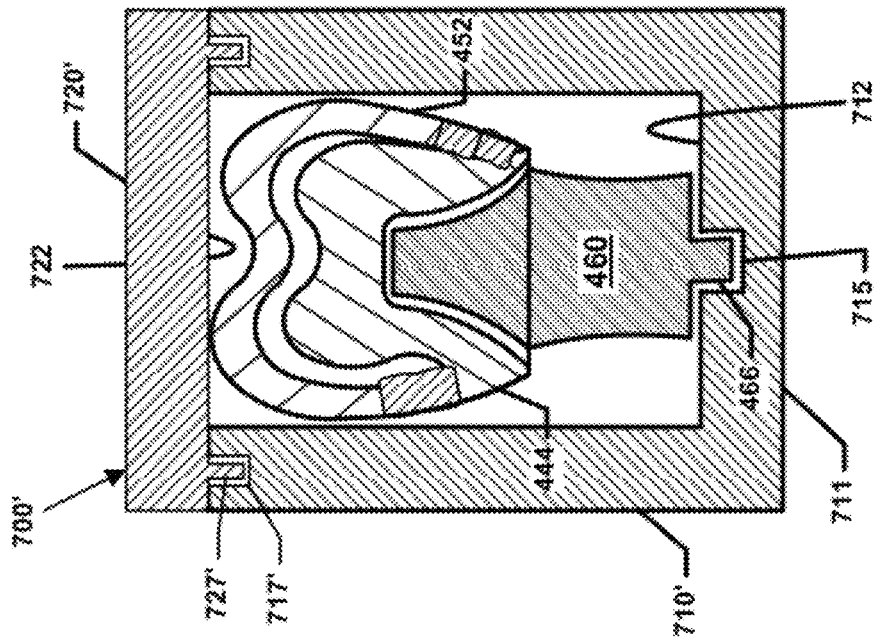
FIG. 12 is a diagram showing a fabrication assembly that includes a customized tooth die suitable for use in the inspection process of FIG. 9 in accordance with the principles of the present disclosure.

FIG. 12 is a diagram showing a fabrication assembly 450 including a customized tooth die 460 having a base 462 with a height H2 that is greater than a height H1 of the original tooth die 460 (see FIG. 7). In other implementations, however, the customized tooth die 460 may have a height that is less than the height H1 of the original tooth die 460. FIG. 13 shows the fabrication assembly 450 with the customized tooth die 460 installed on an example jig 700'. A mounting flange 466 of the tooth die 466 fits within a recess 715 in the seating area 712 of the jig base 710. The height H2 of the tooth die base 462 is sufficient to position the crown pattern 452 at a sufficient distance from the cover 720 when the crown pattern 452 is seated correctly on the dental coping 444. The cover 720' of the example jig 700' includes pegs 727' that fit within openings 717' of the jig base 710'.

Figure 14:
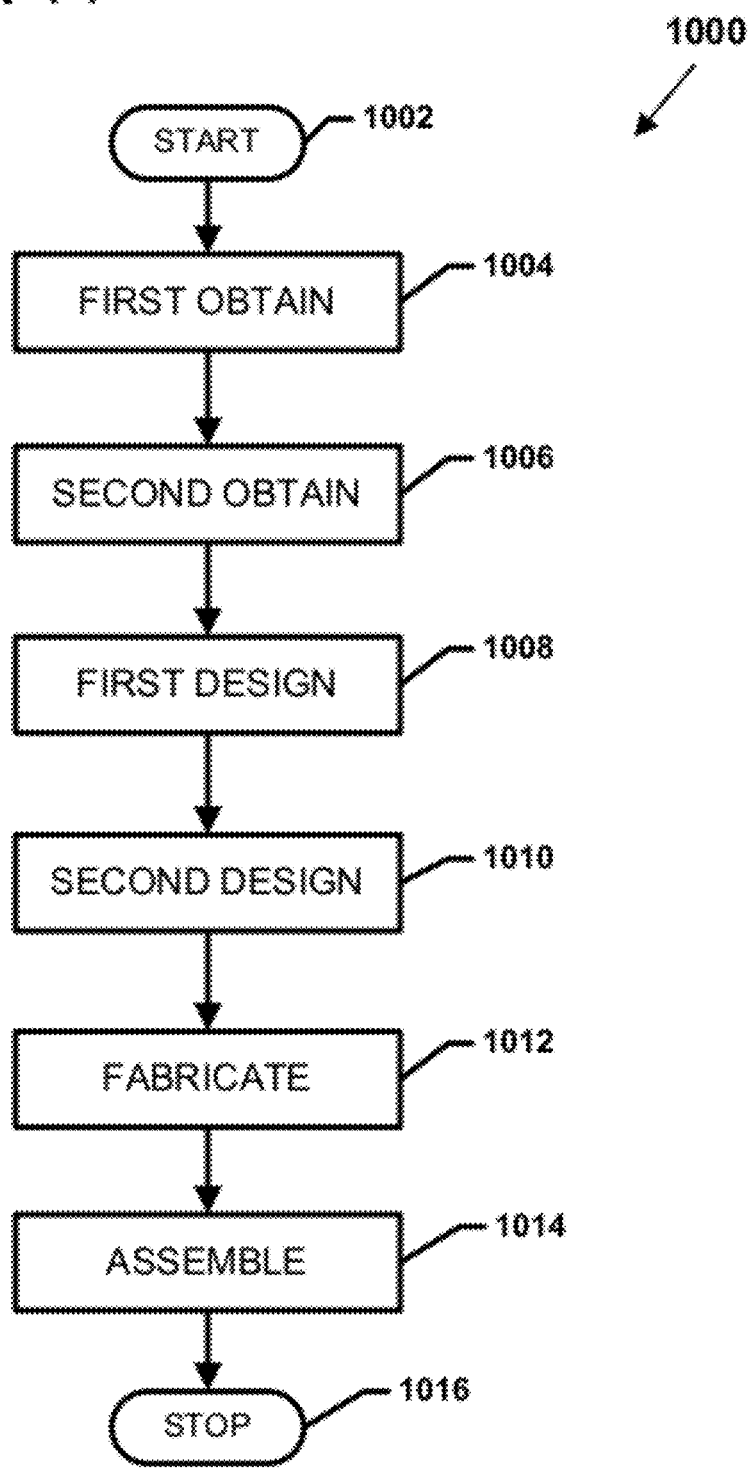
FIG. 14 is a flowchart illustrating an operational flow for an example second customization process in accordance with the principles of the present disclosure.

FIG. 14 is a flowchart illustrating an operational flow for an example second customization process 1000 by which a custom jig 1100 (FIGS. 15-19) can be designed and fabricated for use with a particular fabrication assembly 450 or dental prosthesis 440 to inspect the fabrication assembly 450 or dental prosthesis 440. In accordance with aspects of the disclosure, the second customization process 1000 can be used to implement the second obtain operation 806 of the inspection process 800. The second customization process 1000 performs any appropriate initialization procedures and begins at a start module 1002.

A first obtain operation 1004 acquires or receives the dentition model 200 of the patient. The dentition model 200 includes the prepared tooth, at least one mesial adjacent tooth, at least one distal adjacent tooth, and at least one antagonistic tooth. In some implementations, the dentition model 200 represents the full dentition of the patient. In other implementations, the dentition model 200 represents a partial dentition of the patient (e.g., a half arch, a quarter arch, etc.).

In some implementations, the first obtain operation 1004 pulls the dentition model 200 from computer memory. For example, in some implementations, the dentition prosthesis model 200 can be obtained from a third party, for example, via an electronic network (e.g., the Internet) or via a storage medium (e.g., a hard disk, an optical disc, a flash memory, etc.). In other implementations, the dentition model 200 is generated based on position data of the dentition acquired via a scanner (e.g., intra-oral scanner, line scanner, etc.).

Figure 15:
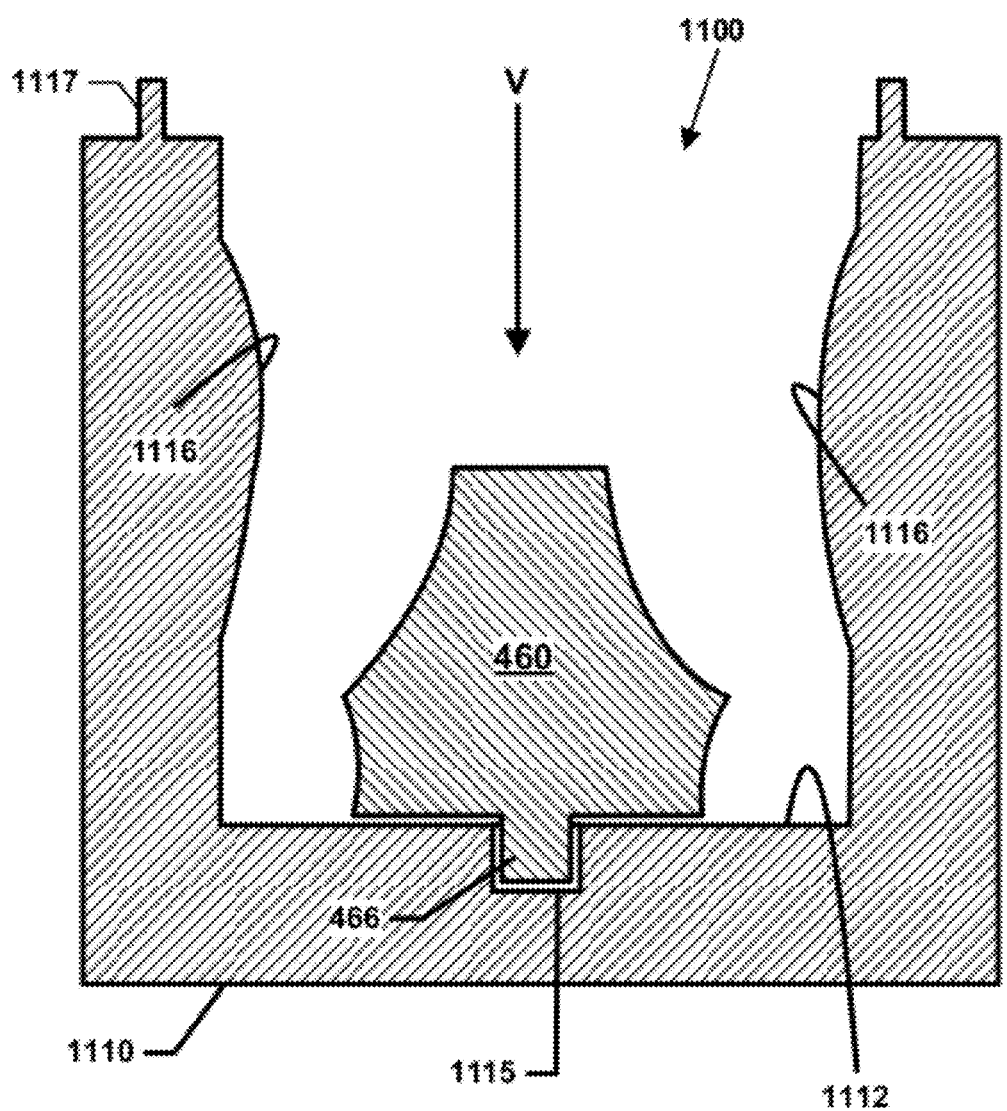
FIG. 15 is a cross-sectional view of a tooth die mounted to a jig base suitable for use in the inspection process of FIG. 9.

A second obtain operation 1006 produces, acquires, or receives a jig base seating area 1112 (see FIG. 15). In some implementations, the second obtain operation 1006 obtains a generic jig base. For example, in one implementation, the second obtain operation 1006 obtains a generic jig base including a flat seating area. In other implementations, the second obtain operation 1006 obtains a generic jig base including a seating area having a keying arrangement (e.g., a peg and hole).

In other implementations, the second obtain operation 1006 creates a jig base customized to a particular dental prosthesis 440 (or tooth die 460). For example, the second obtain operation 1006 can generate or retrieve from memory an electronic model of the jig base from which a jig base 1110 can be fabricated. In certain implementation, the seating area 1112 of the customized jig base 1110 includes a keying arrangement. For example, in one implementation, the second obtain operation 1006 defines a recess 1115 in the jig base seating area 1112 that is shaped to complement a mounting flange 466 on a tooth die 460 (see FIG. 15). In other implementations, the second obtain operation 1006 includes a peg that is shaped to complement a recess defined on the tooth die 460. In one implementation, the keying arrangement is non-uniformly shaped to enable the tooth die 460 to mount to the seating area in only one rotational orientation.

A first design operation 1008 generates one or more electronic models of support members 1114 that are coupled to the jig base 1110. In accordance with some aspects, inward facing surfaces 1116 of the support members 1114 are designed based on contouring of anatomy adjacent to the prepared tooth. For example, in certain implementations, the second design operation 1008 determines a contouring of the mesial adjacent tooth based on the dentition model 200 and applies the contouring to an inward surface 1116A of one of the support members 1114. The first design operation 1008 also determines a contouring of the distal adjacent tooth from the dentition model 200 and applies the contouring to an inward surface 1116B of the other of the support members 1114. In other implementations, one or more of the inward facing surfaces 1116 are flat (e.g., when the tooth does not include an adjacent tooth to one or both sides). In such implementations, the flat inward surfaces 1116 are configured to properly position the prepared tooth within the jig.

The interaction between the support members 1114 and the fabrication assembly 450 or the dental prosthesis 440 may indicate how the dental prosthesis 440 will fit in the patient's mouth. For example, inserting the dental prosthesis 440 between the support members 1114 (e.g., along an insertion vector V) and seating the dental prosthesis 440 on the tooth die 460 may indicate whether the dental prosthesis 440 can be successfully installed on the patient. In one implementation, a technician can modify the size and/or contouring of the fabricated prosthesis 440 (e.g., via grinding, shaving, sanding, etc.) if problems arise when seating the prosthesis 440. In another implementation, the technician can modify the size and/or contouring of the electronic model 300 of the prosthesis 440 and refabricate the prosthesis based on the modified electronic model.

Figure 16:
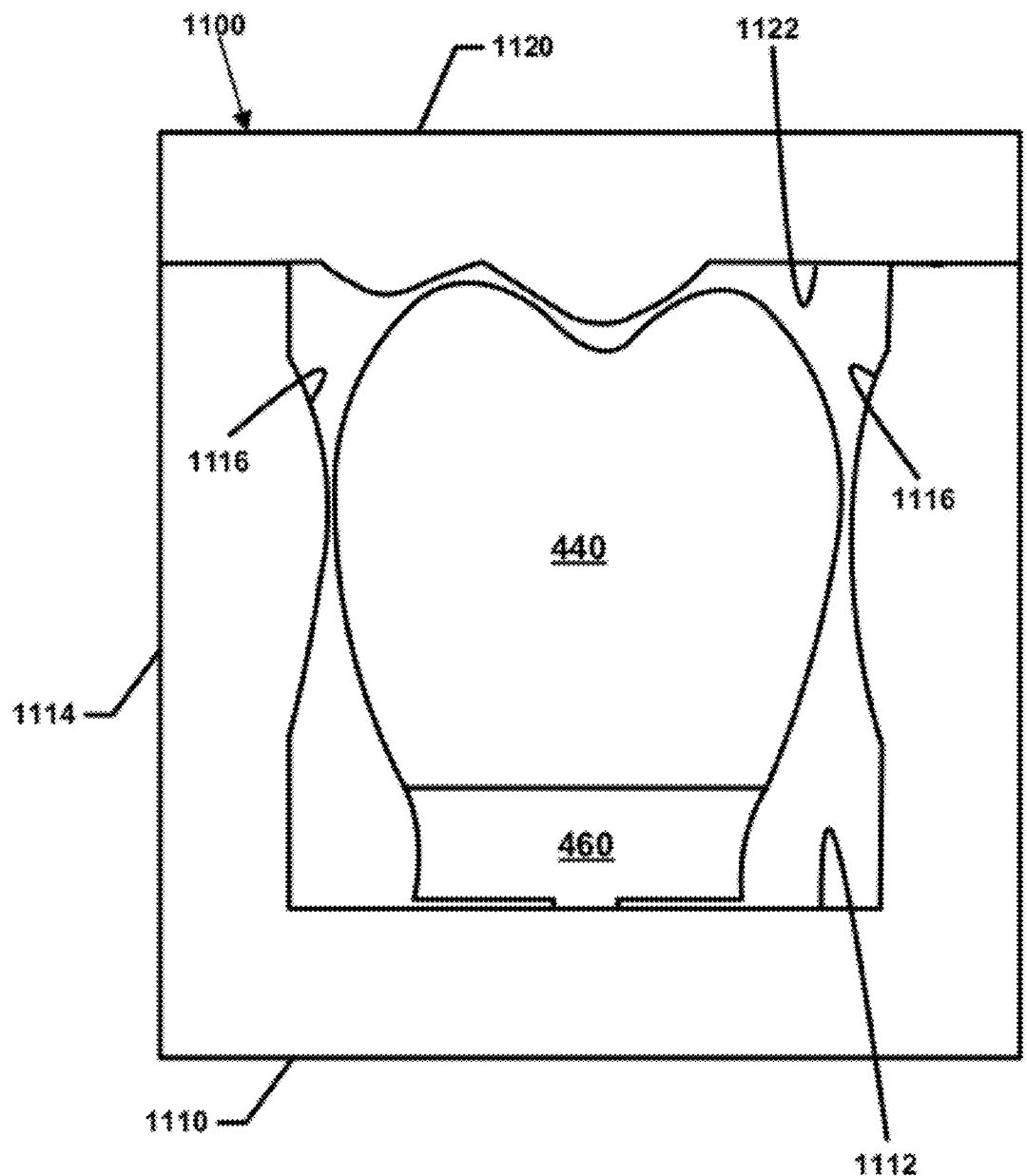
FIG. 16 is a side elevational view of an example dental prosthesis mounted in a customized jig suitable for use in the inspection process of FIG. 9 in accordance with the principles of the present disclosure.

In some implementations, the first design operation 1008 forms the electronic model of the support members 1114 unitarily with an electronic model of the seating area 1112 of the jig base 1110 (e.g., see FIGS. 15 and 16). Accordingly, the support members 1114 and the jig base seating area 1112 can be printed as a single piece. In one such implementation, the tooth die 460 is formed unitarily with the jig base 1110. In other implementations, the first design operation 1008 forms the support members as separate pieces from the jig base seating area (e.g., see FIG. 10). Accordingly, the support members 1114 can be fabricated separately and subsequently assembled to the jig base 1110. Fabricating the support members 1114 separately from the seating area 112 may decrease the fabrication time.

For example, in some implementations, the first design operation 1008 generates the support member electronic model(s) with a first attachment arrangement with which the support members can be coupled to the jig base seating area. In one implementation, the first design operation 1008 adds one or more pegs to the support members to fit within holes defined in the jig base. In another implementation, the first design operation 1008 defines one or more recesses to the support members to fit around pegs or other protrusions extending from the jig base. In other implementations, the first design operation 1008 adds a frame attachment interface 1119 to the support members 1114 that enables the support members to attach to a frame coupled to the jig base as will be described in more detail herein with reference to FIGS. 17-19.

A second design operation 1010 generates an electronic model of a jig cover 1120 (FIG. 16). In accordance with some aspects, the third design operation 1010 determines a contouring of the antagonistic tooth from the dentition model 200 and applies the contouring to the interface surface 1122 of the jig cover 1120. In accordance with other aspects, the interface surface 1122 is flat (e.g., when the tooth does not have an antagonistic tooth). Accordingly, the interaction between the jig cover 1120 and the fabrication assembly 450 or the dental prosthesis 440 also may indicate how the dental prosthesis 440 will fit in the patient's mouth.

In some implementations, the second design operation 1010 forms the jig cover 1120 unitarily with the support members 1114. In other implementations, the second design operation 1010 forms the jig cover 1120 as a separate piece from the support members 1114. For example, in some such implementations, the first and second design operations 1008, 1010 generate a second attachment arrangement with which the jig cover 1120 can be coupled to the support members 1114. In one implementation, the first and second design operations 1008, 1010 add a peg and hole-style attachment arrangement to the support members 1114 and jig cover 1120 (e.g., see FIGS. 10 and 13).

A fabricate operation 1012 produces the customized jig based on the electronic models. For example, in some implementations, the fabricate operation 1012 prints (e.g., rapid prototypes) each piece of the jig from wax, plaster, resin, powdered metal, or other suitable materials. In other implementations, the fabricate operation 1012 mills the jig pieces from metal, Renwood, wax, resin, or other suitable materials. In still other implementations, the fabricate operation 1012 can mill some pieces and print other pieces.

An assemble operation 1014 builds the jig 1100 from the fabricated pieces. In some implementations, the assemble operation 1014 mounts support members 1114 to the seating area 1112 of the jig base 1110 and installs the tooth die 460 at the seating area 1112. Accordingly, the dental prosthesis 440 (or fabrication assembly 450) can be installed on the tooth die 460 along an insertion vector V (FIG. 15) to test how the sides of the dental prosthesis 440 interact with the sides of adjacent anatomy during insertion. In one implementation, the cover 1120 is seated on the support members 1114 after the dental prosthesis 440 (or fabrication assembly 450) is seated on the tooth die 460 during inspection of the dental prosthesis 440 (or fabrication assembly 450).

The customization process 1000 performs any appropriate completion procedures and ends at a stop module 1016.

Figure 17:
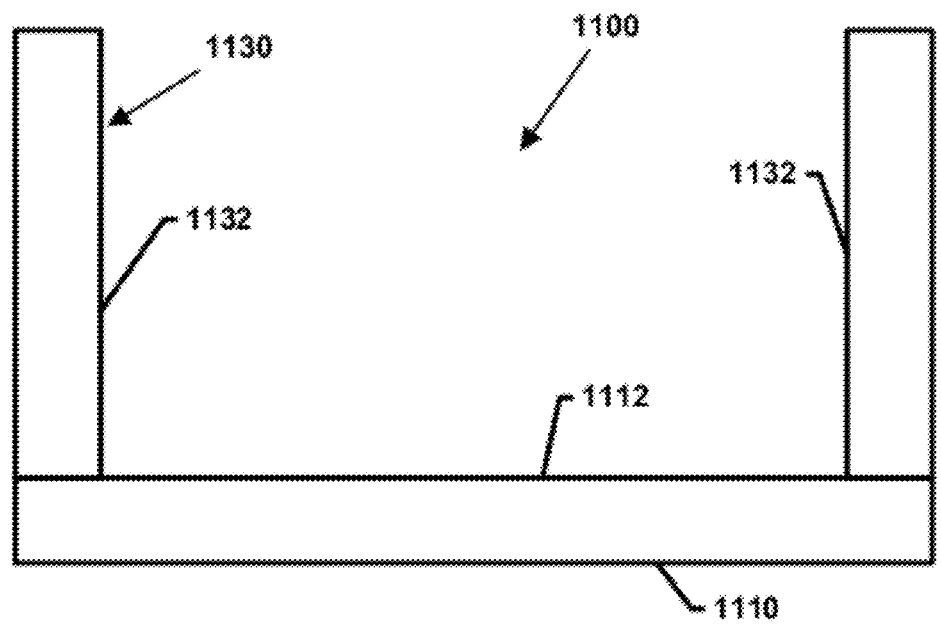
FIG. 17 shows an example jig including a frame suitable for use in the inspection process of FIG. 9 in accordance with the principles of the present disclosure.
Figure 18:
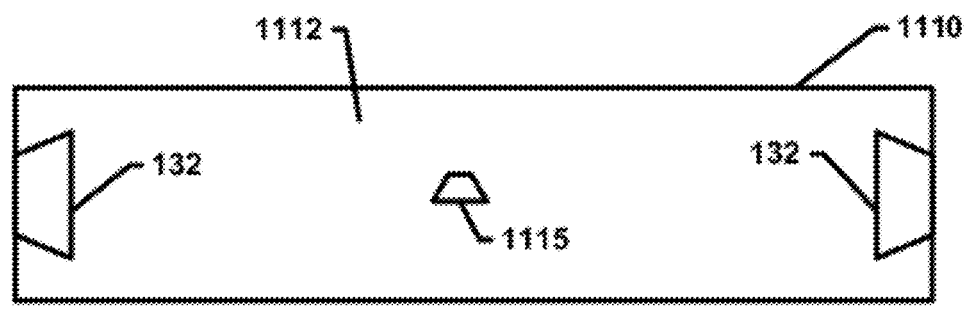
FIG. 18 is a top plan view of FIG. 17 in accordance with the principles of the present disclosure.

Referring to FIGS. 17-20, instead of designing the jig pieces to interconnect via attachment interfaces, the jig can instead include a frame to which one or more pieces of the jig can mount. For example, FIGS. 17 and 18 show an example jig 1100 including a frame 1130. The frame 1130 includes first and second frame members 1132 extending upwardly from opposite sides of the jig base 1110. In certain implementations, multiple frame members 1132 can extend upwardly from each side of the base 1110. A seating area 1112 is defined on the jig base 1110 as described above.

Figure 19:
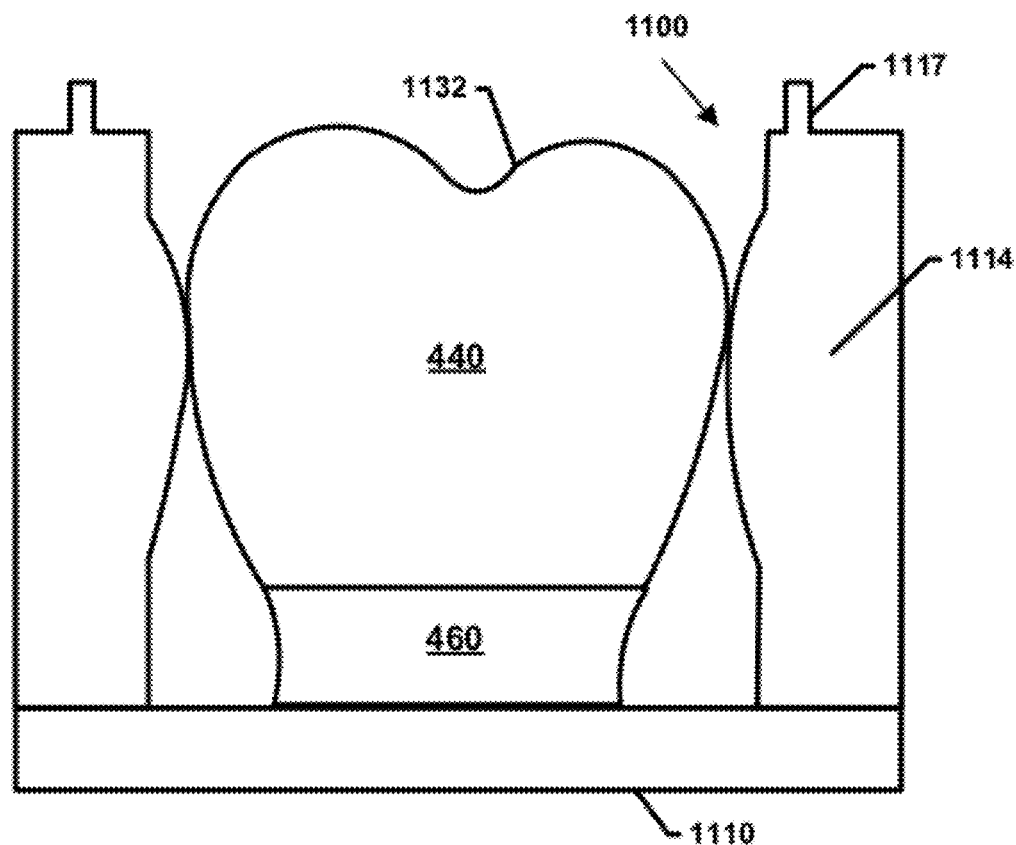
FIG. 19 is a side elevational view of the jig of FIGS. 17 and 18 with jig support members and a dental prosthesis mounted thereto in accordance with the principles of the present disclosure.
Figure 20:
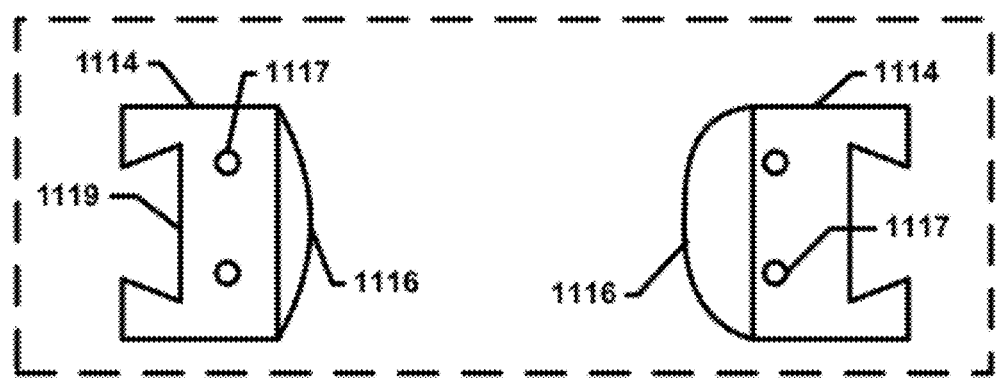
FIG. 20 is a top plan view of the jig support members FIG. 19 in accordance with the principles of the present disclosure.

In accordance with some aspects, the support members 1114 of the jig 1100 can be configured to mount to the frame members 1132 instead of to the jig base 1110 (e.g., see FIG. 19). For example, in some implementations, the support members 1114 can include attachment sections 1119 (FIG. 20) that are configured to fit with at least portions of the frame members 1132. In one implementation, the support members 1114 define attachment sections 1119 that are configured to dove-tail with the frame members 1132 (compare FIGS. 18 and 20). In other implementations, the attachment sections 1119 of the support members 1114 can fit with the frame members 1132 using other types of interlocking configurations.

Figure 21:
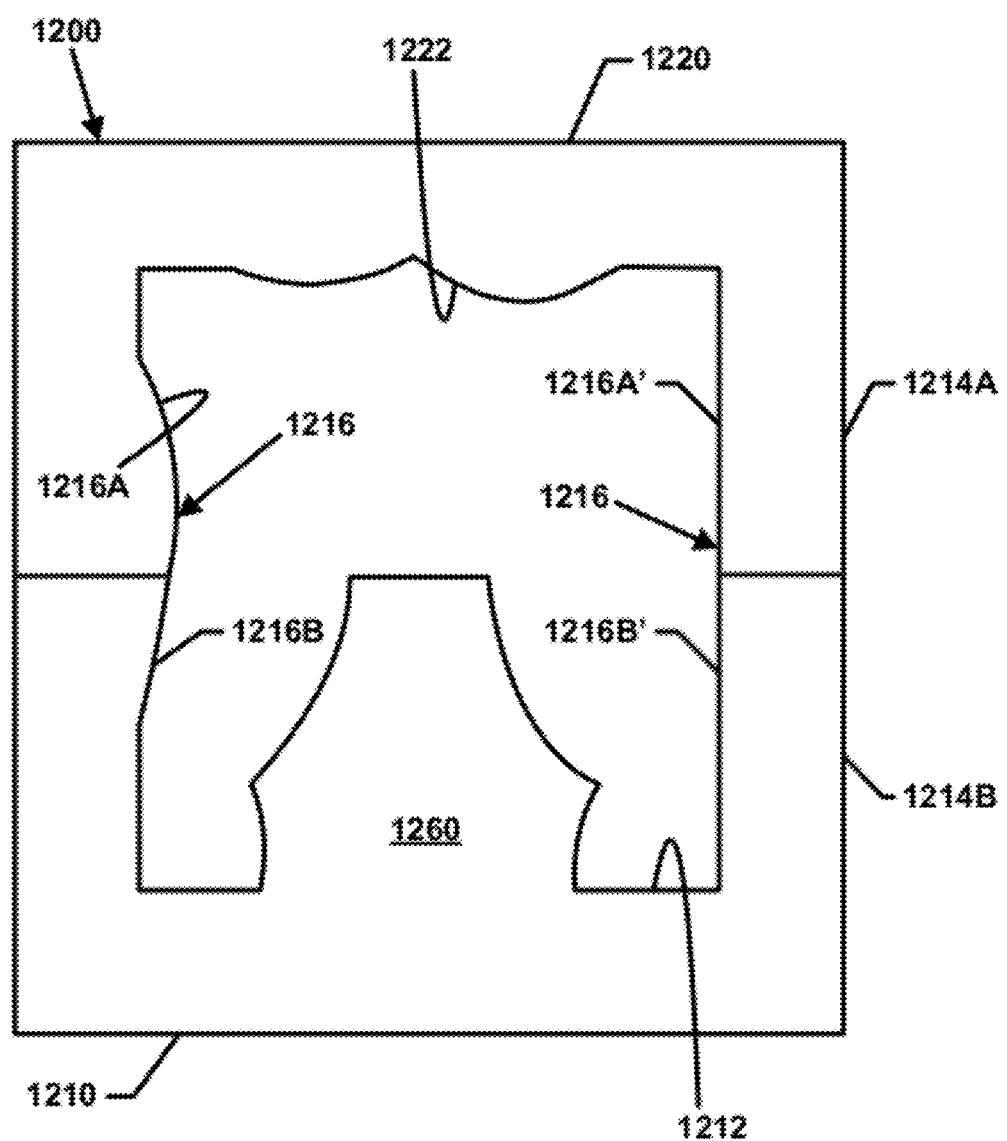
FIG. 21 shows yet another example jig that is suitable for inspecting a dental appliance or pattern thereof.

FIG. 21 shows yet another example jig 1200 that is suitable for inspecting a dental appliance or pattern thereof. The jig 1200 includes a cover member 1220 mounted to a base 1210. In accordance with some aspects, one or more of the inner surfaces of the jig 1200 define contours of adjacent anatomical structures (e.g., an adjacent tooth, an antagonistic tooth, etc.) as discussed above. For example, in FIG. 21, the left sidewall 1216 of the jig 1200 defines one side of an adjacent tooth and the cover member inner surface 1222 defines an occlusal surface of an antagonistic tooth.

In accordance with other aspects, however, the sidewalls and antagonistic surfaces of certain types of jigs may not define such contours. For example, in FIG. 21, the right sidewall of the jig 1200 is generally flat. A flat sidewall may be designed and formed when the appliance is to be installed in a dentition that does not have adjacent anatomy on that side. In other implementations, the cover inner surface 1222, the left sidewall, the right sidewall, or some combination thereof may be flat. The flat sidewalls are designed and constructed to provide adequate structure to support the cover member 1220 when the cover 1220 is mounted to the jig base 1210.

In accordance with some aspects of the disclosure, the base 1210 of the jig 1200 defines a portion 1216B of the side walls 1216 of the jig 1200 and the cover member 1220 defines another portion 1216A of the side walls 1216 of the jig 1200. For example, the base 1210 may form a first portion 1216B of each sidewall 1216 and the cover 1220 may form a second portion 1216A of each sidewall 1216. The cover 1220 mounts to the jig base 1210 by interfacing the side wall portions 1216A, 1216B together.

In some implementations, the sidewall portions 1216B of the base 1210 include pegs or other protrusions 1217 that fit within openings defined in the cover member 1220. In other implementations, the sidewall portions 1216A of the cover 1220 include pegs or other protrusions 1227 that fit within openings defined in the base 1210. In still other implementations, both the base 1210 and the cover 1220 define protrusions and openings. In still other implementations, the sidewall portions 1216A, 1216B are otherwise connected together.

In some implementations, the jig base portions 1216B of the sidewalls 1216 form about half of the sidewalls 1216 and the cover member portions 1216A form about half of the sidewalls 1216. In other implementations, the jig base portions 1216B of the sidewalls 1216 form a majority of the sidewalls 1216 and the cover member portions 1216A form a minority of the sidewalls 1216. In other implementations, the jig base portions 1216B of the sidewalls 1216 form a minority of the sidewalls 1216 and the cover member portions 1216A form a majority of the sidewalls 1216.

In accordance with other implementations, the example jig 1200 includes a tooth die 1260 that is monolithic with the base 1210 of the jig 1200. For example, the tooth die 1260 can be fabricated (e.g., printed) monolithically with the jig base 1210 based on an electronic model of the jig 1200 and tooth die 1260. In some implementations, the jig base portions 1216B of the sidewalls 1216 of the jig 1200 extend to about the same height of the tooth die 1260 (see FIG. 21). In one implementation, the height of the tooth die 1260 is measured along an insertion axis of a dental appliance or pattern thereof onto the tooth die 1260. In other implementations, tops of the jig base portions 1216B of the sidewalls 1216 can be higher or lower than a top of the tooth die 1260.

Figure 22:
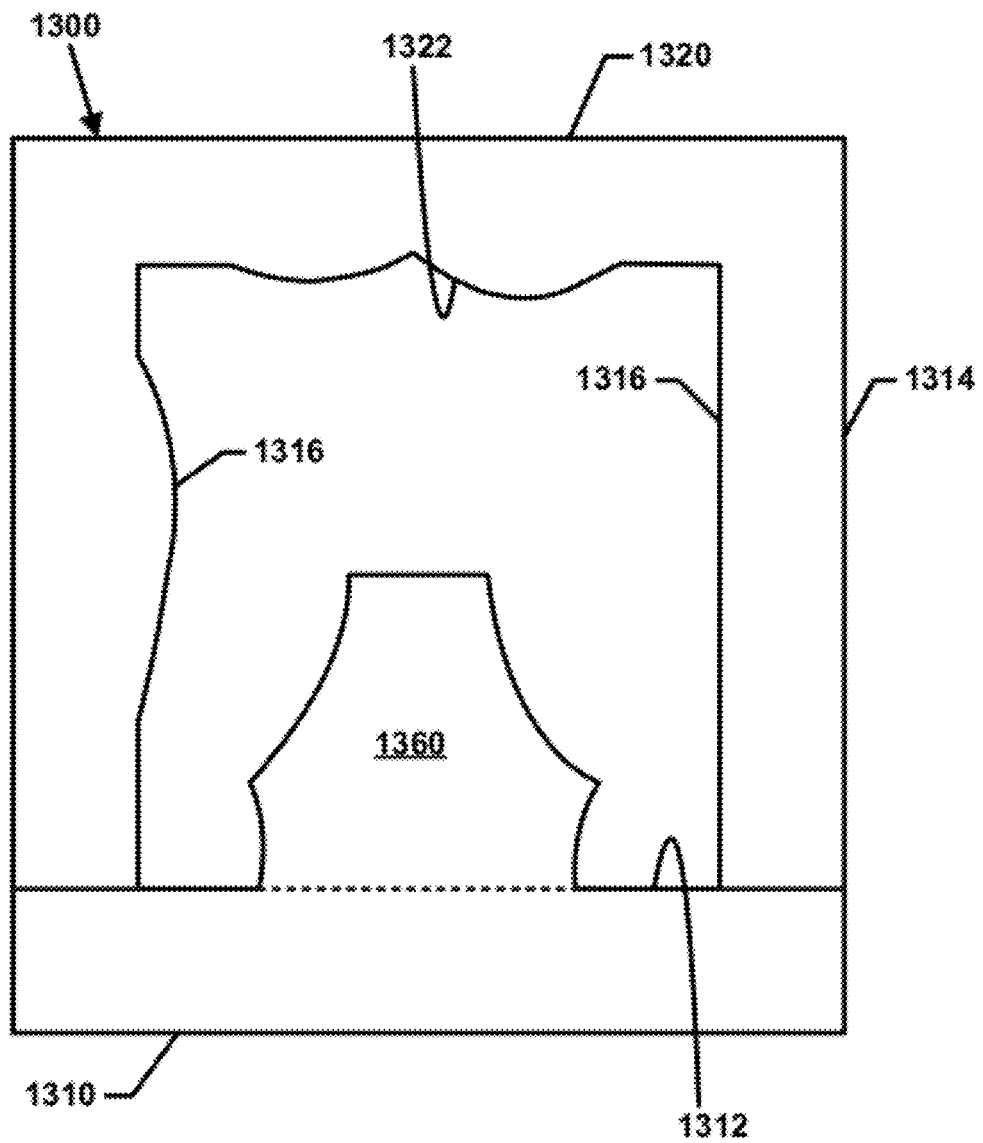
FIG. 22 shows yet another example jig that is suitable for inspecting a dental appliance or pattern thereof.

FIG. 22 shows yet another example jig 1300 that is suitable for inspecting a dental appliance or pattern thereof. The jig 1300 includes a cover member 1320 mounted to a base 1310.

In accordance with some aspects, one or more of the inner surfaces of the jig 1300 define contours of adjacent anatomical structures (e.g., an adjacent tooth, an antagonistic tooth, etc.) as discussed above. For example, in FIG. 22, the left sidewall 1316 of the jig 1300 defines one side of an adjacent tooth and the cover member inner surface 1322 defines an occlusal surface of an antagonistic tooth. In the example shown, the right sidewall 1316 does not define contours of an adjacent tooth. In other implementations, however, the right sidewall may define such contours, the left sidewall may define a flat surface, or the cover member inner surface 1322 may define a flat surface.

In accordance with some aspects of the disclosure, the cover member 1320 of the jig 1300 defines the side walls 1316 of the jig 1300. For example, the base 1310 may form a first interface (e.g., a protrusion or opening) that is configured to interact with an interface (e.g., a protrusion or opening) on the bottom of the side walls 1316. Accordingly, the cover 1320 mounts to the jig base 1310 by interfacing the side wall portions 1316 with the base 1310.

In accordance with some implementations, the example jig 1300 includes a tooth die 1360 that is monolithic with the base 1310 of the jig 1300. For example, the tooth die 1360 can be fabricated (e.g., printed) monolithically with the jig base 1310 based on an electronic model of the jig 1300 and tooth die 1360. In accordance with other implementations, the tooth die 1360 is manufactured separately from the base 1310. In some such implementations, the tooth die 1360 includes an interface (e.g., a protrusion or opening) configured to interact with a corresponding interface (e.g., a protrusion or opening) on the base 1310. In other such implementations, the tooth die 1360 is configured to seat on the base 1310 without locking to the base 1310.

Figure 23:
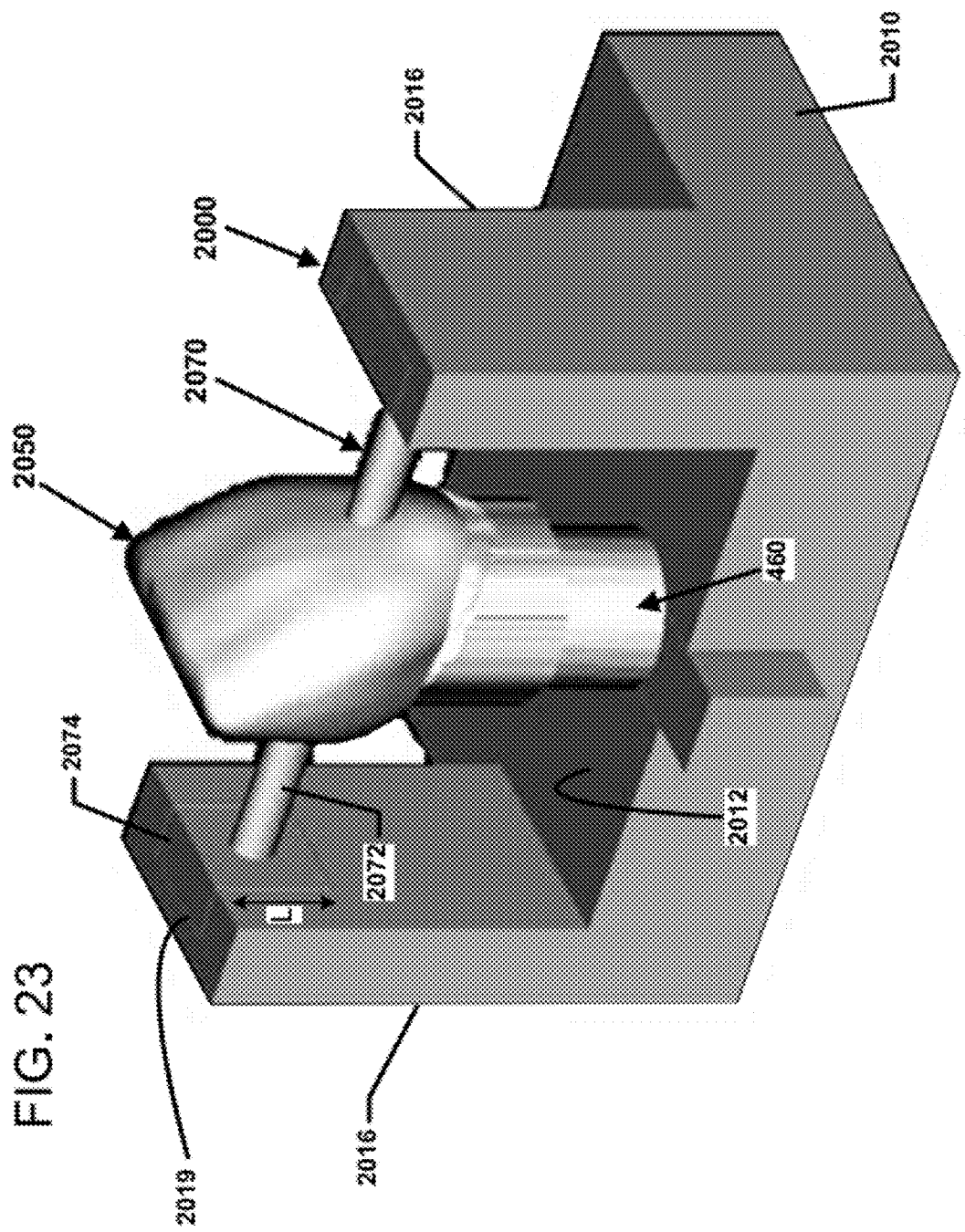
FIG. 23 is a perspective view showing another example inspection system for determining whether a pattern of a dental prosthesis fits on a tooth die or fabricated coping.

FIG. 23 is a perspective view showing another example inspection system for determining whether a pattern 2050 of a dental prosthesis (e.g., a crown) fits on a fabricated coping or customized tooth die 460. As noted above, the tooth die 460 defines a preparation site on which the dental prosthesis is intended to seat. In certain implementations, the tooth die 460 is a customized tooth die having a specified height as described above.

The inspection system includes a jig 2000 having a base 2010 defining a surface 2012 at which the tooth die 460 can be mounted. In some implementations, the tooth die 460 mounts to the base 2011 using any of the interface arrangements described above (e.g., tab and slot, protrusion and hole, dovetails, etc.). In certain implementations, the tooth die 460 fits on the base 2011 only at a predetermine orientation.

The jig 2000 also includes side walls 2016 protruding upwardly from the base 2010. In some implementations, the sidewalls 2016 are monolithic with the base 2010. In other implementations, the sidewalls 2016 are separate pieces mounted to the base 2010. For example, the sidewalls 2016 may include interface arrangements that interlock or otherwise fit with interface arrangements on the base 2010. In other implementations, the sidewalls 2016 may be mounted to rails (e.g., via dovetailing) extending from the base 2010.

Each of the sidewalls 2016 of the jig 2000 defines a slot 2019 extending downwardly from a top of the sidewall 2016. In some implementations, a length L of the slot 2019 extends downwardly from the top of the sidewall 2016 over less than half the height of the sidewall 2016. In other implementations, the slot 2019 may have a length L extending over a majority of the height of the sidewall 2016. In certain implementations, the length L is selected to position a pattern 2050 at an appropriate height on the tooth die 460.

The inspection system also includes a mounting arrangement 2070 coupled to the pattern 2050. The mounting arrangement 2070 includes at least one protrusion 2072 extending from an outer surface of the pattern 2050. In the example shown, two protrusions 2072 extend from generally opposite sides of the pattern 2050. In other implementations, the mounting arrangement 2070 may include additional protrusions 2072 extending in different directions. In some implementations, the protrusions 2072 are generally cylindrical. In other implementations, the protrusions 2072 are fin-shaped.

In some implementations, distal ends of the protrusions 2072 include slides 2074 that are sized and configured to fit within the slots 2019 in the sidewalls 2016. In the example shown, the slides 2074 are block-shaped. In other implementations, the slides 2074 may define any shape suitable for fitting within the slots 2019 (e.g., wedge-shaped, triangular-shaped, rhombus-shaped, semi-circular, etc.). In other implementations, the distal ends of the protrusions 2072, themselves, fit within the slots 2019.

In certain implementations, the protrusions 2072 and slides 2074 are positioned, sized, and oriented to position the pattern 2050 on the jig 2000 at a desired location relative to the tooth die 460 that is also mounted to the jig 2000.

One process for designing such an inspection system includes an obtain operation for obtaining an electronic model of a tooth die 460 and an obtain operation for obtaining an electronic model of a dental prosthesis to be fabricated. For example, a technician may design the electronic model of the tooth die 460 and/or the electronic model of the prosthesis based on positional data representing a dentition of a patient. The electronic model of the prosthesis is designed to fit with the electronic model of the tooth die 460 so that an interior surface of the prosthesis is spaced an appropriate amount from and positioned at an appropriate orientation relative to the tooth die 460.

Figure 24:
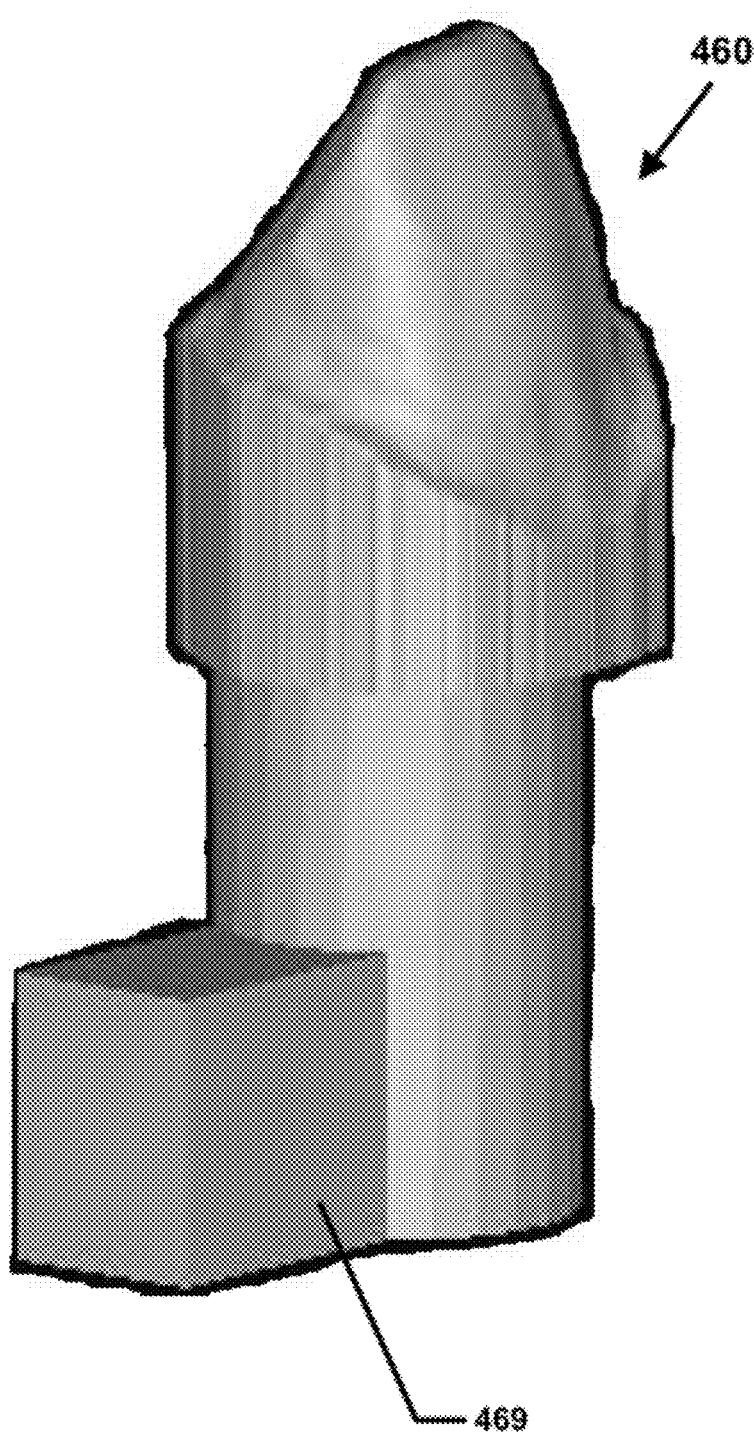
FIG. 24 is a perspective view of an electronic model of example tooth die and key in accordance with the principles of the present disclosure.
Figure 25:
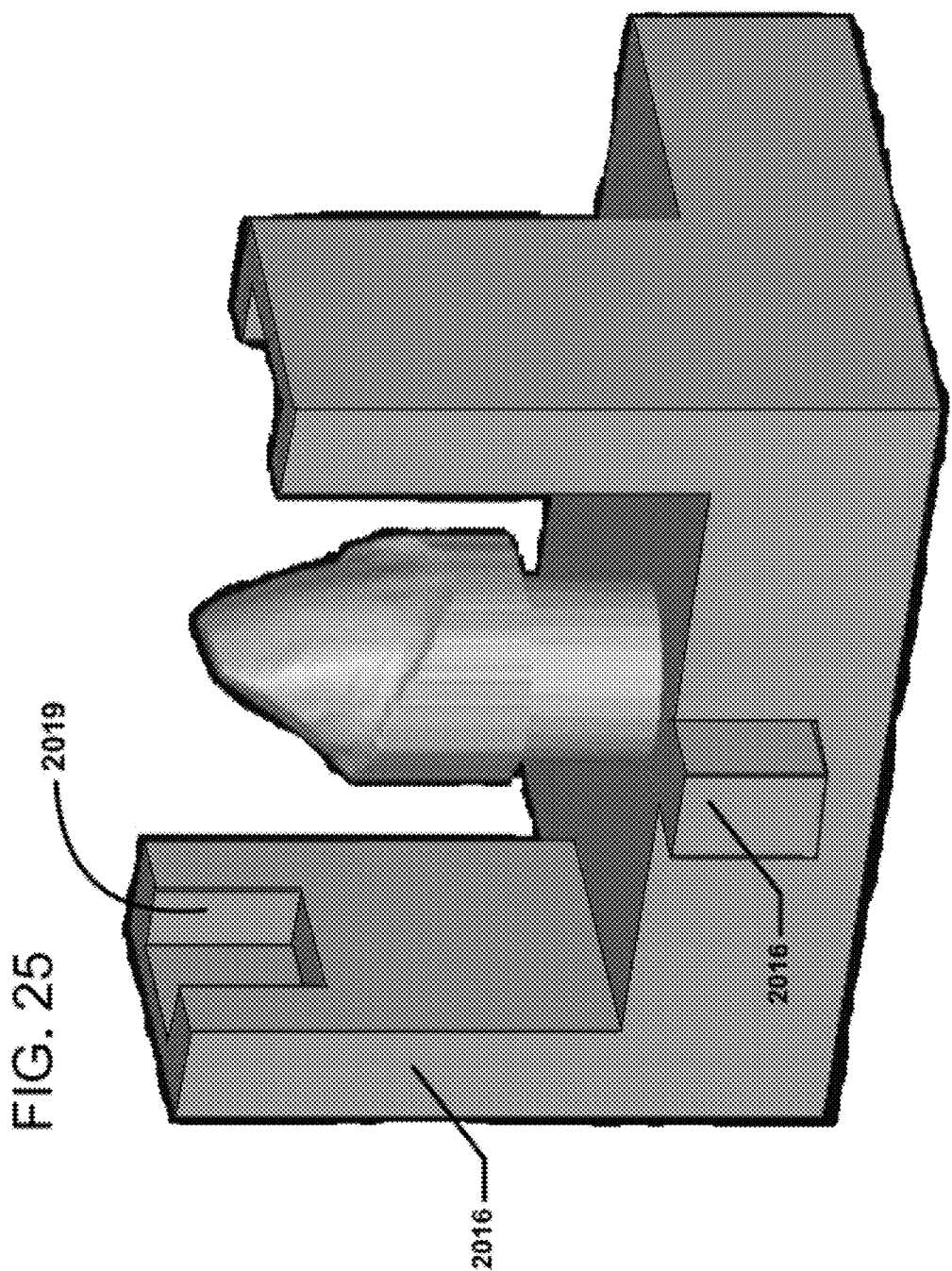
FIG. 25 is a perspective view of an electronic model of an example jig on which the tooth die of FIG. 24 is mounted.
Figure 26:
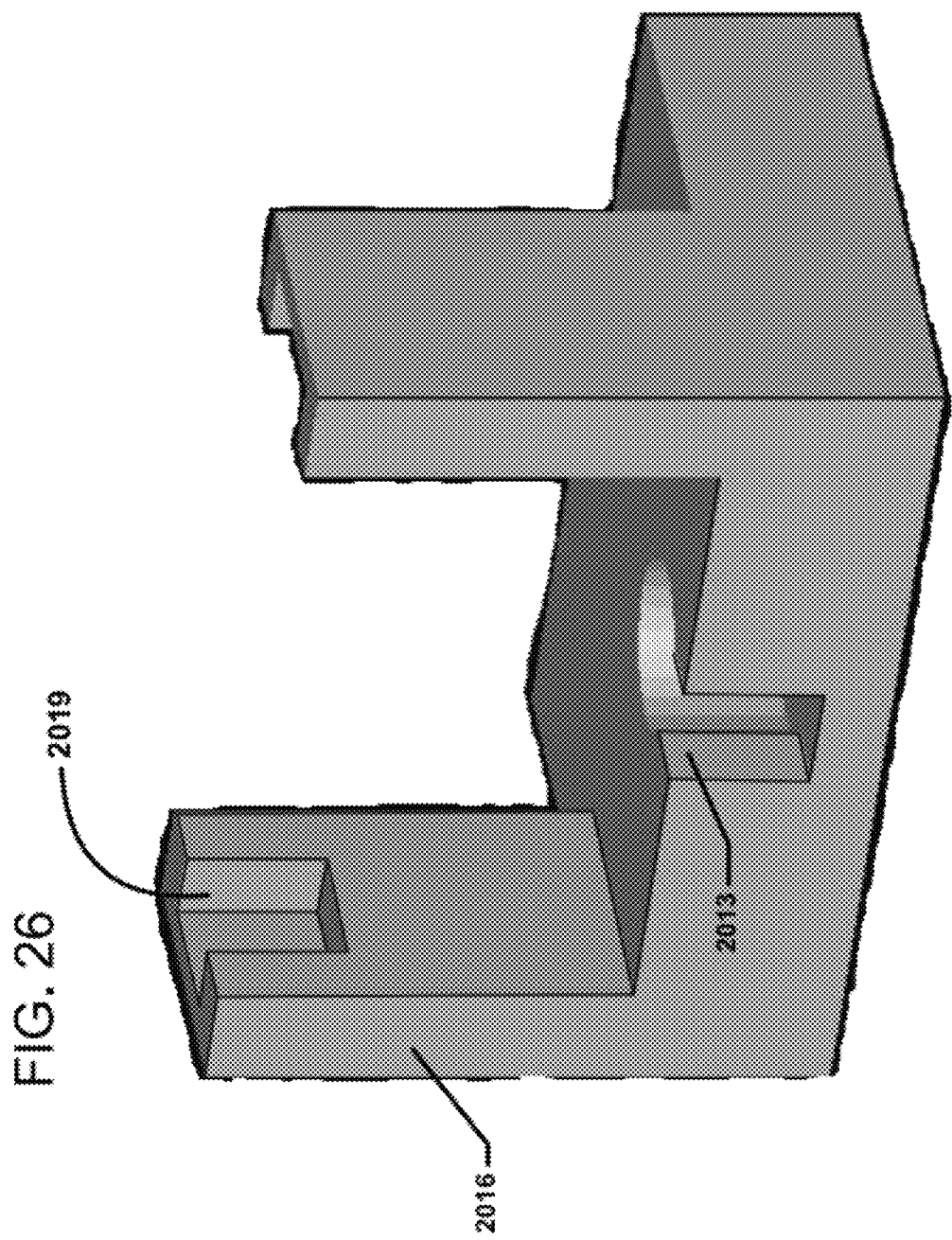
FIG. 26 is a perspective view of an electronic model of the example jig of FIG. 25.
Figure 27:
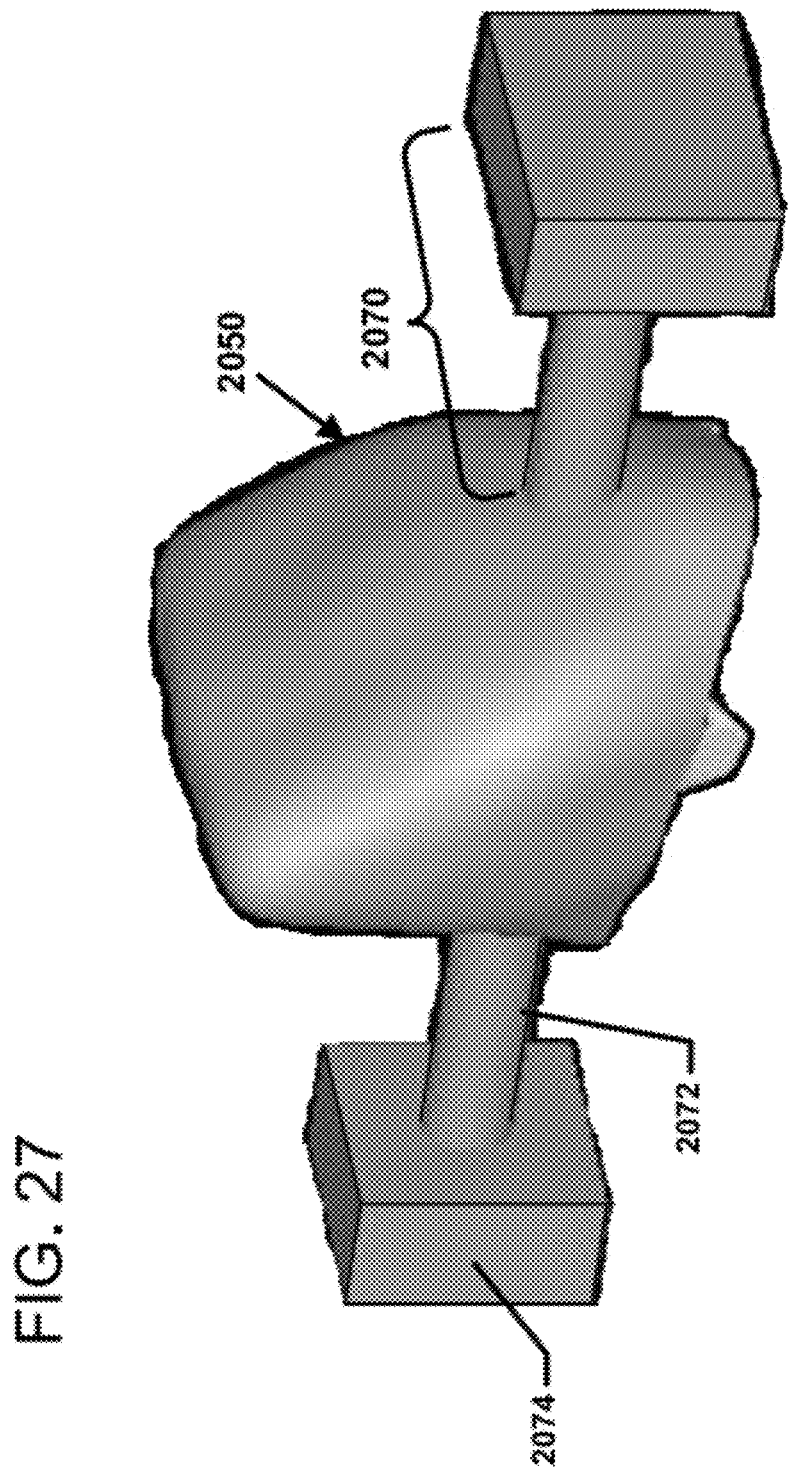
FIG. 27 shows an electronic model of a pattern of a prosthesis including an example mounting arrangement in accordance with the principles of the present disclosure.

In some implementations, the technician adds a key 469 to the electronic model of the tooth die (see FIG. 24) so that the tooth die 460 will mount to the base 2010 in only one orientation (see FIG. 25). For example, the key 469 may fit in a keyway 2013 (FIG. 26) defined in the base 2010 in only one orientation. The technician also will add a mounting arrangement 2070 to the electronic model of the prosthesis and fabricated a pattern 2050 of the prosthesis based on the electronic model (see FIG. 27). The pattern 2050 includes the mounting arrangement 2070. The mounting arrangement 2070 is positioned and oriented on the pattern so that the pattern 2050 will seat properly on the tooth die 460 when protrusions 2072 of the mounting arrangement fit into slots 2019 of a jig 2000. In certain implementations, the tooth dies 460, patterns 2050, and mounting arrangements 2070 each may be customized to work with a common jig 2000.

One process for utilizing such an inspection system includes mounting a tooth die 460 to a jig 2000; inserting a pattern 2050 over the tooth die 460 including fitting a mounting arrangement 2070 of the pattern 2050 with the jig 2000. In some implementations, the tooth die 460 is a customized tooth die. In some implementations, the pattern 2050 represents a dental crown. In other implementations, the pattern 2050 represents a dental coping.

In some implementations, fitting the mounting arrangement with the jig 2000 includes inserting one or more mounting members 2072 protruding from the pattern 2050 into slots 2019 defined by the jig 2000. In certain implementations, inserting the mounting members 2072 includes sliding at least a part of mounting members 2072 into slots 2019 defined in the sidewalls 2016. For example, in certain implementations, inserting the mounting arrangement includes inserting slides 2074 at distal ends of the mounting members 2072 into the slots 2019.

It is noted that the terms "first" and "second" when used to refer to process steps are not intended to convey an order in which the steps need be implemented. Rather, the terms "first" and "second" are used for ease of explanation. For example, in some implementations of inspection process 800, the second mount operation 808 can be implemented prior to the first mount operation 808 (e.g., when the fabrication assembly 450 is mounted without the tooth die 510 or when the tooth die 510 does not include flange 516).

The invention claimed is:

1. A method for manufacturing a dental prosthesis including a coping and a crown, the method comprising:
    obtaining an electronic model of the dental prosthesis including an electronic model of the crown seated on an electronic model of the coping;
    determining a height of the dental prosthesis based on the electronic model of the dental prosthesis when the electronic model of the crown is positioned appropriately on the electronic model of the coping to simulate a proper seating of the crown on the coping;
    obtaining a coping fabricated based on the electronic model of the coping;
    obtaining a pattern of the crown based on the electronic model of the crown;
    obtaining an electronic model of a preparation die;
    determining a suitable height for the preparation die based on the height of the dental prosthesis and a height of a seating jig;
    modifying the electronic model of the preparation die to have the determined suitable height;
    fabricating the preparation die with the determined suitable height based on the electronic model of the preparation die;
    forming a manufacturing arrangement including mounting the coping on the preparation die and mounting the pattern of the crown on the coping;
    mounting the manufacturing arrangement on the seating jig; and
    analyzing a relationship between the manufacturing arrangement and the seating jig to determine whether the pattern of the crown is seated appropriately on the coping.

2. The method of claim 1, further comprising sealing the pattern of the crown to the coping when the crown is determined to be seated appropriately on the coping.

3. The method of claim 2, further comprising:
    forming a first mold from the manufacturing arrangement after waxing the pattern to the coping; and
    pressing the crown using the first mold to form the dental prosthesis.

4. The method of claim 1, wherein obtaining the coping comprises:
    printing a pattern of the coping based on the electronic model of the coping;
    forming a second mold of the coping based on the pattern; and
    casting the coping using the second mold.

5. The method of claim 1, wherein obtaining the coping comprises milling the coping based on the electronic model of the coping.

6. The method of claim 1, wherein obtaining an electronic model of the preparation die comprises:
    scanning the preparation site with an intra-oral scanner to obtain positional data; and
    generating the electronic model of the preparation die based on the positional data.

7. The method of claim 1, wherein obtaining an electronic model of a preparation die comprises:
    scanning a physical model of a preparation site to obtain positional data; and
    generating the electronic model of the preparation die based on the positional data.

8. The method of claim 1, wherein mounting the manufacturing arrangement on the jig comprises:
    seating the preparation die of the manufacturing arrangement on a base of the jig; and
    placing a cover on the base of the jig over the manufacturing arrangement.

9. The method of claim 8, wherein analyzing the relationship between the manufacturing arrangement and the jig comprises determining whether an occlusal surface of the crown pattern of the manufacturing arrangement is located more than a tolerated distance away from the cover.

10. The method of claim 9, further comprising raising the pattern of the crown off the coping if the occlusal surface is below the cover by more than the tolerated distance.

* * * * *